(12) United States Patent
Bojarski et al.

(10) Patent No.: US 9,314,235 B2
(45) Date of Patent: Apr. 19, 2016

(54) TISSUE ANCHOR AND INSERTION TOOL

(75) Inventors: Raymond A. Bojarski, Attleboro, MA (US); George Sikora, Bridgewater, MA (US)

(73) Assignee: SMITH & NEPHEW, INC., Memphis, TN (US)

( * ) Notice: Subject to any disclaimer, the term of this patent is extended or adjusted under 35 U.S.C. 154(b) by 1149 days.

(21) Appl. No.: 10/358,252

(22) Filed: Feb. 5, 2003

(65) Prior Publication Data

US 2004/0153074 A1 Aug. 5, 2004

(51) Int. Cl.
*A61B 17/04* (2006.01)

(52) U.S. Cl.
CPC ......... *A61B 17/0401* (2013.01); *A61B 17/0487* (2013.01); *A61B 2017/044* (2013.01); *A61B 2017/0409* (2013.01); *A61B 2017/0412* (2013.01); *A61B 2017/0414* (2013.01); *A61B 2017/0424* (2013.01); *A61B 2017/0427* (2013.01); *A61B 2017/0438* (2013.01); *A61B 2017/0445* (2013.01); *A61B 2017/0458* (2013.01)

(58) Field of Classification Search
USPC ......... 606/72–73, 75, 99, 104, 232, 233, 139, 606/151, 300–301, 310–315, 321, 916, 144, 606/145, 148, 187; 227/119; 470/164; 72/391.2–391.6; 408/139; 600/3, 7
See application file for complete search history.

(56) References Cited

U.S. PATENT DOCUMENTS

| 233,475 A | 10/1880 | Cook et al. |
|---|---|---|
| 261,501 A | 7/1882 | Vandermark |
| 1,260,264 A * | 3/1918 | Huszar .............................. 30/130 |
| 1,635,066 A | 7/1927 | Wells |
| 2,269,963 A * | 1/1942 | Wappler .......................... 604/61 |
| 2,479,464 A | 8/1949 | Bliss |

(Continued)

FOREIGN PATENT DOCUMENTS

| EP | 0 108 912 | 5/1984 |
|---|---|---|
| EP | 0 260 970 | 3/1988 |

(Continued)

OTHER PUBLICATIONS

Annex to Form PCT/ISA/206 Communication Relating to the Results of the Partial International Search (6 pages).

(Continued)

*Primary Examiner* — David Isabella
*Assistant Examiner* — Christine Nelson
(74) *Attorney, Agent, or Firm* — Burns & Levinson LLP; Joseph M. Maraia

(57) ABSTRACT

A surgical tool includes a shaft for receiving implants. The shaft defines a non-linear track. The tool includes a deployment member movable along the track to deploy the implants. An implant includes a body, and a plurality of alternating threads and flutes helically arranged about the body such that the body rotates under a linear applied force. Alternatively, an implant includes a body having a distal end for pound-in advancement into tissue. The body includes a plurality of cone-shaped, stacked barbs. A surgical tool includes two implants. The first implant has forward threads and the second implant has reverse threads. The first implant has threads for rotary advancement into tissue and the second implant is configured for pound-in advancement into tissue. The first and second implants are configured for pound-in advancement into tissue.

10 Claims, 14 Drawing Sheets

(56) References Cited

U.S. PATENT DOCUMENTS

| | | | |
|---|---|---|---|
| 2,610,631 A | 9/1952 | Calicchio | |
| 2,880,728 A | 4/1959 | Rights | |
| 2,881,762 A | 4/1959 | Lowrie | |
| 3,011,185 A * | 12/1961 | Khachigian | 470/96 |
| 3,409,014 A | 11/1968 | Grant | |
| 3,470,875 A | 10/1969 | Johnson | |
| 3,618,447 A | 11/1971 | Goins | |
| 3,664,345 A | 5/1972 | Dabbs et al. | |
| 3,716,058 A | 2/1973 | Tanner, Jr. | |
| 3,752,516 A | 8/1973 | Mumma | |
| 3,752,519 A | 8/1973 | Nordell et al. | |
| 3,757,629 A | 9/1973 | Schneider | |
| 3,825,010 A | 7/1974 | McDonald | |
| 3,840,017 A | 10/1974 | Violante | |
| 3,842,824 A | 10/1974 | Neufeld | |
| 3,842,840 A | 10/1974 | Schweizer | |
| 3,867,944 A | 2/1975 | Samuels | |
| 3,871,379 A | 3/1975 | Clarke | |
| 3,910,281 A | 10/1975 | Kletschka et al. | |
| 3,946,740 A | 3/1976 | Bassett | |
| 3,976,079 A | 8/1976 | Samuels et al. | |
| 3,977,050 A | 8/1976 | Perez | |
| 3,985,138 A | 10/1976 | Jarvik | |
| 4,006,747 A | 2/1977 | Kronenthal et al. | |
| 4,039,753 A | 8/1977 | Balogh et al. | |
| 4,086,914 A * | 5/1978 | Moore | 600/7 |
| 4,141,087 A | 2/1979 | Shalaby et al. | |
| 4,144,876 A | 3/1979 | DeLeo | |
| 4,160,453 A * | 7/1979 | Miller | 606/187 |
| 4,186,514 A | 2/1980 | Oquita | |
| 4,235,238 A | 11/1980 | Ogiu et al. | |
| 4,316,469 A | 2/1982 | Kapitanov | |
| 4,326,531 A | 4/1982 | Shimonaka | |
| 4,493,323 A | 1/1985 | Albright et al. | |
| 4,505,274 A | 3/1985 | Speelman | |
| 4,531,522 A | 7/1985 | Bedi et al. | |
| 4,534,350 A | 8/1985 | Golden et al. | |
| 4,570,623 A | 2/1986 | Ellison et al. | |
| 4,595,007 A | 6/1986 | Mericle | |
| 4,596,249 A | 6/1986 | Freda et al. | |
| 4,602,635 A | 7/1986 | Mulhollan et al. | |
| 4,616,650 A | 10/1986 | Green et al. | |
| 4,624,254 A | 11/1986 | McGarry et al. | |
| 4,635,637 A | 1/1987 | Schreiber | |
| 4,636,121 A | 1/1987 | Miller | |
| 4,641,652 A | 2/1987 | Hutterer et al. | |
| 4,662,068 A | 5/1987 | Polonsky | |
| 4,705,040 A | 11/1987 | Mueller et al. | |
| 4,719,917 A | 1/1988 | Barrows et al. | |
| 4,723,540 A | 2/1988 | Gilmer, Jr. | |
| 4,724,839 A | 2/1988 | Bedi et al. | |
| 4,741,330 A | 5/1988 | Hayhurst | |
| 4,741,336 A | 5/1988 | Failla et al. | |
| 4,750,492 A | 6/1988 | Jacobs | |
| 4,760,848 A | 8/1988 | Hasson | |
| 4,781,190 A | 11/1988 | Lee | |
| 4,809,695 A | 3/1989 | Gwathmey et al. | |
| 4,823,794 A | 4/1989 | Pierce | |
| 4,841,960 A | 6/1989 | Garner | |
| 4,846,793 A * | 7/1989 | Leonard et al. | 604/62 |
| 4,858,608 A | 8/1989 | McQuilkin | |
| 4,873,976 A | 10/1989 | Schreiber | |
| 4,884,572 A | 12/1989 | Bays et al. | |
| 4,887,601 A | 12/1989 | Richards | |
| 4,890,615 A | 1/1990 | Caspari et al. | |
| 4,895,148 A | 1/1990 | Bays et al. | |
| 4,899,743 A | 2/1990 | Nicholson et al. | |
| 4,917,699 A | 4/1990 | Chervitz | |
| 4,923,461 A | 5/1990 | Caspari et al. | |
| 4,950,285 A | 8/1990 | Wilk | |
| 4,961,741 A | 10/1990 | Hayhurst | |
| 4,983,176 A | 1/1991 | Cushman et al. | |
| 4,988,243 A * | 1/1991 | Proffitt | 408/241 R |
| 4,994,028 A | 2/1991 | Leonard et al. | |
| 5,037,422 A | 8/1991 | Hayhurst | |
| 5,041,129 A | 8/1991 | Hayhurst et al. | |
| 5,046,513 A | 9/1991 | Gatturna et al. | |
| 5,053,047 A | 10/1991 | Yoon | |
| 5,059,201 A | 10/1991 | Asnis | |
| 5,078,731 A | 1/1992 | Hayhurst | |
| 5,084,050 A | 1/1992 | Draenert | |
| 5,084,058 A | 1/1992 | Li | |
| 5,087,263 A | 2/1992 | Li | |
| 5,100,415 A | 3/1992 | Hayhurst | |
| 5,102,421 A * | 4/1992 | Anspach, Jr. | 606/232 |
| 5,123,913 A | 6/1992 | Wilk et al. | |
| 5,141,520 A | 8/1992 | Goble et al. | |
| 5,149,329 A | 9/1992 | Richardson | |
| 5,154,189 A | 10/1992 | Oberlander | |
| D331,626 S | 12/1992 | Hayhurst | |
| 5,178,629 A | 1/1993 | Kammerer | |
| 5,203,787 A | 4/1993 | Noblitt et al. | |
| 5,207,753 A * | 5/1993 | Badrinath | 606/96 |
| 5,211,650 A | 5/1993 | Noda | |
| 5,217,470 A | 6/1993 | Weston | |
| 5,219,359 A | 6/1993 | McQuilkin et al. | |
| 5,224,946 A | 7/1993 | Hayhurst et al. | |
| 5,234,426 A | 8/1993 | Rank et al. | |
| 5,236,445 A | 8/1993 | Hayhurst et al. | |
| 5,246,441 A | 9/1993 | Ross et al. | |
| 5,258,015 A | 11/1993 | Li et al. | |
| 5,258,016 A * | 11/1993 | DiPoto et al. | 606/232 |
| 5,261,914 A | 11/1993 | Warren | |
| 5,268,001 A * | 12/1993 | Nicholson et al. | 606/232 |
| 5,269,809 A | 12/1993 | Hayhurst et al. | |
| 5,279,539 A | 1/1994 | Bohan et al. | |
| 5,282,809 A | 2/1994 | Kammerer et al. | |
| 5,318,577 A | 6/1994 | Li | |
| 5,320,633 A | 6/1994 | Allen et al. | |
| 5,336,229 A | 8/1994 | Noda | |
| 5,336,231 A | 8/1994 | Adair | |
| 5,342,369 A | 8/1994 | Harryman, II | |
| 5,354,299 A | 10/1994 | Coleman | |
| 5,364,408 A | 11/1994 | Gordon | |
| 5,405,354 A * | 4/1995 | Sarrett | 606/148 |
| 5,417,691 A | 5/1995 | Hayhurst | |
| 5,417,692 A * | 5/1995 | Goble et al. | 606/73 |
| 5,437,680 A | 8/1995 | Yoon | |
| 5,439,467 A * | 8/1995 | Benderev et al. | 606/139 |
| 5,439,684 A | 8/1995 | Prewett et al. | |
| 5,441,502 A | 8/1995 | Bartlett | |
| 5,447,512 A | 9/1995 | Wilson et al. | |
| 5,458,081 A | 10/1995 | Reichert | |
| 5,458,608 A | 10/1995 | Wortrich | |
| 5,467,786 A | 11/1995 | Allen et al. | |
| 5,474,572 A | 12/1995 | Hayhurst | |
| 5,490,750 A | 2/1996 | Gundy | |
| 5,496,331 A | 3/1996 | Xu et al. | |
| 5,500,000 A * | 3/1996 | Feagin et al. | 606/232 |
| 5,501,692 A * | 3/1996 | Riza | 606/148 |
| 5,520,696 A | 5/1996 | Wenstrom, Jr. | |
| 5,520,700 A * | 5/1996 | Beyar et al. | 606/139 |
| 5,520,921 A | 5/1996 | Chalifoux | |
| 5,522,820 A | 6/1996 | Caspari et al. | |
| 5,522,844 A | 6/1996 | Johnson | |
| 5,527,342 A | 6/1996 | Pietrzak et al. | |
| 5,545,178 A | 8/1996 | Kensey et al. | |
| 5,554,171 A | 9/1996 | Gatturna et al. | |
| 5,562,684 A | 10/1996 | Kammerer | |
| 5,573,286 A | 11/1996 | Rogozinski | |
| 5,593,424 A | 1/1997 | Northrup, III | |
| 5,601,557 A | 2/1997 | Hayhurst | |
| 5,601,558 A | 2/1997 | Torrie et al. | |
| 5,607,432 A | 3/1997 | Fucci | |
| 5,609,597 A | 3/1997 | Lehrer | |
| 5,641,256 A | 6/1997 | Gundy | |
| 5,643,319 A * | 7/1997 | Green et al. | 606/218 |
| 5,643,321 A | 7/1997 | McDevitt | |
| 5,647,874 A | 7/1997 | Hayhurst | |
| 5,658,299 A * | 8/1997 | Hart | 606/139 |
| 5,665,112 A | 9/1997 | Thal | |
| 5,690,676 A | 11/1997 | DiPoto et al. | |
| 5,690,678 A | 11/1997 | Johnson | |
| 5,702,422 A | 12/1997 | Stone | |

(56) References Cited

U.S. PATENT DOCUMENTS

| | | | |
|---|---|---|---|
| 5,702,462 A | 12/1997 | Oberlander | |
| 5,713,904 A | 2/1998 | Errico et al. | |
| 5,716,359 A | 2/1998 | Ojima et al. | |
| 5,720,753 A * | 2/1998 | Sander et al. | 606/104 |
| 5,720,765 A | 2/1998 | Thal | |
| 5,725,529 A | 3/1998 | Nicholson et al. | |
| 5,725,556 A | 3/1998 | Moser et al. | |
| 5,725,581 A | 3/1998 | Branemark | |
| 5,728,109 A | 3/1998 | Schulze et al. | |
| 5,728,136 A | 3/1998 | Thal | |
| 5,730,744 A | 3/1998 | Justin et al. | |
| 5,746,754 A | 5/1998 | Chan | |
| 5,749,898 A | 5/1998 | Schulze et al. | |
| 5,782,862 A | 7/1998 | Bonutti | |
| 5,782,864 A | 7/1998 | Lizardi | |
| 5,797,928 A | 8/1998 | Kogasaka | |
| 5,810,848 A | 9/1998 | Hayhurst | |
| 5,814,069 A | 9/1998 | Schulze et al. | |
| RE36,020 E * | 12/1998 | Moore et al. | 606/144 |
| 5,843,084 A | 12/1998 | Hart et al. | |
| 5,843,087 A | 12/1998 | Jensen et al. | |
| 5,846,254 A | 12/1998 | Schulze et al. | |
| 5,860,983 A | 1/1999 | Wenstrom, Jr. | |
| 5,871,490 A | 2/1999 | Schulze et al. | |
| 5,891,168 A | 4/1999 | Thal | |
| 5,893,592 A | 4/1999 | Schulze et al. | |
| 5,893,856 A | 4/1999 | Jacob et al. | |
| 5,893,880 A | 4/1999 | Egan et al. | |
| 5,895,395 A | 4/1999 | Yeung | |
| 5,897,564 A | 4/1999 | Schulze et al. | |
| 5,902,321 A | 5/1999 | Caspari et al. | |
| 5,921,986 A | 7/1999 | Bonutti | |
| 5,928,244 A * | 7/1999 | Tovey et al. | 606/104 |
| 5,938,668 A * | 8/1999 | Scirica et al. | 606/145 |
| 5,941,439 A | 8/1999 | Kammerer et al. | |
| 5,948,002 A | 9/1999 | Bonutti | |
| 5,954,747 A | 9/1999 | Clark | |
| 5,964,765 A | 10/1999 | Fenton, Jr. | |
| 5,964,783 A | 10/1999 | Grafton et al. | |
| 5,976,127 A | 11/1999 | Lax | |
| 5,980,524 A | 11/1999 | Justin et al. | |
| 5,989,252 A | 11/1999 | Fumex | |
| 5,993,458 A | 11/1999 | Vaitekunas et al. | |
| 6,024,758 A | 2/2000 | Thal | |
| 6,027,523 A | 2/2000 | Schmieding | |
| 6,039,753 A | 3/2000 | Meislin | |
| 6,045,574 A | 4/2000 | Thal | |
| 6,056,320 A * | 5/2000 | Khalifa et al. | 280/805 |
| 6,063,106 A | 5/2000 | Gibson | |
| 6,066,146 A | 5/2000 | Carroll et al. | |
| 6,074,395 A | 6/2000 | Trott et al. | |
| 6,096,038 A * | 8/2000 | Michelson | 606/86 A |
| 6,096,060 A | 8/2000 | Fitts et al. | |
| 6,117,160 A | 9/2000 | Bonutti | |
| 6,143,017 A | 11/2000 | Thal | |
| 6,146,387 A | 11/2000 | Trott et al. | |
| 6,152,934 A | 11/2000 | Harper et al. | |
| 6,152,936 A | 11/2000 | Christy et al. | |
| 6,156,039 A | 12/2000 | Thal | |
| 6,165,203 A | 12/2000 | Krebs | |
| 6,174,324 B1 | 1/2001 | Egan et al. | |
| 6,193,754 B1 | 2/2001 | Seedhom | |
| 6,217,591 B1 | 4/2001 | Egan et al. | |
| 6,283,996 B1 | 9/2001 | Chervitz et al. | |
| 6,286,746 B1 | 9/2001 | Egan et al. | |
| 6,306,158 B1 | 10/2001 | Bartlett | |
| 6,306,159 B1 | 10/2001 | Schwartz et al. | |
| 6,319,263 B1 | 11/2001 | Levinson | |
| 6,319,271 B1 | 11/2001 | Schwartz et al. | |
| 6,358,271 B1 | 3/2002 | Eagan et al. | |
| 6,409,743 B1 | 6/2002 | Fenton, Jr. | |
| 6,432,123 B2 | 8/2002 | Schwartz et al. | |
| 6,491,707 B2 | 12/2002 | Makower et al. | |
| 6,500,184 B1 | 12/2002 | Chan et al. | |
| 6,520,980 B1 | 2/2003 | Foerster | |
| 6,524,317 B1 | 2/2003 | Richart et al. | |
| 6,527,795 B1 | 3/2003 | Lizardi | |
| 6,533,802 B2 | 3/2003 | Bojarski et al. | |
| 6,554,852 B1 | 4/2003 | Oberlander | |
| 6,585,730 B1 | 7/2003 | Foerster | |
| 6,635,073 B2 | 10/2003 | Bonutti | |
| 6,641,596 B1 * | 11/2003 | Lizardi | 606/232 |
| 6,652,563 B2 | 11/2003 | Dreyfuss | |
| 6,656,182 B1 | 12/2003 | Hayhurst | |
| 6,669,705 B2 | 12/2003 | Westhaver et al. | |
| 6,692,499 B2 * | 2/2004 | Tormala et al. | 606/72 |
| 6,692,516 B2 | 2/2004 | West, Jr. et al. | |
| 6,770,076 B2 | 8/2004 | Foerster | |
| 6,855,157 B2 | 2/2005 | Foerster et al. | |
| 6,923,824 B2 | 8/2005 | Morgan et al. | |
| 6,972,019 B2 * | 12/2005 | Michelson | 606/86 A |
| 6,972,027 B2 | 12/2005 | Fallin et al. | |
| 7,153,312 B1 * | 12/2006 | Torrie et al. | 606/144 |
| 7,163,563 B2 | 1/2007 | Schwartz et al. | |
| 7,252,630 B2 * | 8/2007 | Terwilliger et al. | 600/3 |
| 7,500,983 B1 | 3/2009 | Kaiser et al. | |
| 2001/0010005 A1 | 7/2001 | Kammerer et al. | |
| 2002/0019649 A1 * | 2/2002 | Sikora et al. | 606/232 |
| 2002/0052629 A1 | 5/2002 | Morgan et al. | |
| 2002/0091959 A1 | 7/2002 | Klein et al. | |
| 2002/0095181 A1 | 7/2002 | Beyar | |
| 2002/0133159 A1 | 9/2002 | Jackson | |
| 2002/0147463 A1 | 10/2002 | Martinek | |
| 2002/0156500 A1 | 10/2002 | Storz-Irion et al. | |
| 2002/0165548 A1 | 11/2002 | Jutley | |
| 2002/0173821 A1 | 11/2002 | Fenton et al. | |
| 2003/0070004 A1 * | 4/2003 | Mukundan et al. | 709/330 |
| 2003/0109900 A1 | 6/2003 | Martinek | |
| 2003/0120277 A1 * | 6/2003 | Berger | 606/73 |
| 2003/0130694 A1 | 7/2003 | Bojarski et al. | |
| 2003/0236555 A1 | 12/2003 | Thornes | |
| 2004/0002734 A1 * | 1/2004 | Fallin et al. | 606/232 |
| 2004/0037094 A1 | 2/2004 | Muegge et al. | |
| 2004/0092937 A1 | 5/2004 | Criscuolo et al. | |
| 2004/0133238 A1 * | 7/2004 | Cerier | 606/232 |
| 2004/0133239 A1 | 7/2004 | Singhatat | |
| 2004/0138683 A1 * | 7/2004 | Shelton et al. | 606/151 |
| 2004/0243131 A1 | 12/2004 | Dirks et al. | |
| 2004/0267317 A1 * | 12/2004 | Higgins et al. | 606/232 |
| 2005/0033363 A1 | 2/2005 | Bojarski et al. | |
| 2005/0037150 A1 | 2/2005 | Iijima et al. | |
| 2005/0143761 A1 * | 6/2005 | Modesitt et al. | 606/148 |
| 2005/0187577 A1 | 8/2005 | Selvitelli et al. | |
| 2005/0277961 A1 | 12/2005 | Stone et al. | |
| 2005/0277986 A1 | 12/2005 | Foerster et al. | |
| 2006/0190042 A1 | 8/2006 | Stone et al. | |
| 2007/0083236 A1 | 4/2007 | Sikora et al. | |
| 2008/0065114 A1 | 3/2008 | Stone et al. | |
| 2008/0082128 A1 | 4/2008 | Stone | |

FOREIGN PATENT DOCUMENTS

| | | |
|---|---|---|
| EP | 0 315 371 | 5/1989 |
| EP | 0 598 219 | 5/1994 |
| EP | 0 632 999 A1 | 1/1995 |
| EP | 0 847 727 | 6/1996 |
| EP | 0 913 123 | 5/1999 |
| EP | 1 013 229 | 6/2000 |
| EP | 1 444 959 | 8/2004 |
| EP | 1 568 326 | 10/2007 |
| FR | 2 422 386 | 4/1978 |
| FR | 2 731 610 | 9/1996 |
| JP | 54-166092 | 11/1979 |
| JP | 54-166093 | 11/1979 |
| JP | 54-176284 | 11/1979 |
| JP | 54-178988 | 11/1979 |
| JP | 09-507770 A | 8/1997 |
| WO | WO 98/22047 | 5/1998 |
| WO | 98/51241 | 11/1998 |
| WO | WO 99/01084 | 1/1999 |
| WO | WO 99/12480 | 3/1999 |
| WO | 00/40159 | 7/2000 |
| WO | WO 01/39671 | 6/2001 |
| WO | 01/39671 | 7/2001 |

(56) References Cited

FOREIGN PATENT DOCUMENTS

| WO | WO 02/36020 | 5/2002 |
|----|----|----|
| WO | WO 02/091959 | 11/2002 |
| WO | 03/001893 A2 | 1/2003 |
| WO | WO 2004/037094 | 5/2004 |
| WO | WO 2005/037150 | 4/2005 |
| WO | 2005065553 A1 | 7/2005 |

OTHER PUBLICATIONS

Thal, R. "A Knotless Suture Anchor & Method for Arthroscopic Bankart Repair Introduction," Poster Board No. 296 at the 1999 Annual Meeting of the American Academy of Orthopaedic Surgeons.
Unicorn Surgical Sutures & Suture Needles, Suture Needles Information:, 2005.
U.S. Appl. No. 60/114,170, filed Dec. 30, 1998; Schwartz et al.
Office Action U.S. Appl. No. 10/278,474 dated Mar. 30, 2007, 21 pages.
Office Action U.S. Appl. No. 10/278,474 dated Aug. 30, 2007, 10 pages.
Office Action U.S. Appl. No. 10/278,474 dated Aug. 14, 2008, 14 pages.
Office Action U.S. Appl. No. 10/278,474 dated Jan. 22, 2008, 9 pages.
Office Action U.S. Appl. No. 10/278,474 dated Dec. 29, 2008, 9 pages.
Office Action U.S. Appl. No. 10/618,445 dated May 25, 2006, 42 pages.
Office Action U.S. Appl. No. 10/918,445 dated Oct. 12, 2006, 25 pages.
Office Action U.S. Appl. No. 10/918,445 dated Mar. 6, 2007, 11 pages.
Office Action U.S. Appl. No. 10/918,445 dated Jun. 27, 2007, 13 pages.
Office Action U.S. Appl. No. 10/918,445 dated Dec. 28, 2007, 12 pages.
Office Action U.S. Appl. No. 10/918,445 dated Jul. 24, 2008, 16 pages.
Office Action U.S. Appl. No. 11/165,551 dated Feb. 25, 2008, 15 pages.
Office Action U.S. Appl. No. 11/165,551 dated Oct. 28, 2008, 13 pages.
Office Action U.S. Appl. No. 11/535,868 dated May 23, 2008, 14 pages.
Office Action U.S. Appl. No. 11/535,868 dated Nov. 12, 2008, 18 pages.
Office Action from European Serial No. 01981796.4 mailed Apr. 21, 2005.
PCT/US2004/003258 Annex to Form PCT/ISA/203 Communication Relating to the Results of the Partial International Search, mailed Jul. 30, 2004, 6 pages.
PCT/US2004/003528 International Search Report, mailed Oct. 21, 2004, 10 pages.
PCT/US2006/024752 International Preliminary Report on Patentability, dated Jan. 10, 2008.
PCT/US2006/024752 International Search Report and Written Opinion, dated Nov. 7, 2006.
PCT/US2007/076348 International Search Report and Written Opinion, dated Jun. 20, 2008.
Non-Final Office Action mailed Mar. 31, 2009 for U.S. Appl. No. 10/918,445.
Notice of Reasons of Rejection for Japanese Application No. 2009-530498, mailed Jun. 19, 2012.
Notification of Reason for Rejection for Japanese Application No. 2011-039140, mailed Sep. 26, 2012.
Examiner's First Report on Australian Application No. 2007345245, mailed May 22, 2012.
Office Action issued in U.S. Appl. No. 11/165,551, dated Jun. 2, 2009.
Office Action issued in U.S. Appl. No. 11/535,868, dated May 22, 2009.
Office Action issued in U.S. Appl. No. 11/535,868, dated Mar. 14, 2011.
Office Action issued in U.S. Appl. No. 11/535,868, dated Mar. 24, 2010.
Office Action issued in U.S. Appl. No. 12/684,722, dated Oct. 20, 2011, 8 pages.
Office Action issued in U.S. Appl. No. 12/684,722, dated Feb. 7, 2012.
Office Action issued in U.S. Appl. No. 12/684,752, dated Jan. 25, 2012.
Communication Pursuant to Article 94(3) EPC for European Application 04708599.8, dated Feb. 18, 2008.
Communication Pursuant to Article 94(3) EPC for European Application 04708599.8, dated Apr. 30, 2009.
Communication Pursuant to Article 94(3) EPC for European Application 04708599.8, dated Feb. 28, 2011.
Annex to Form PCT/ISA/206 Communication Relating to the Results of the Partial International Search (6 pgs) Jul. 30, 2004.
PCT/US2006/024752 International Preliminary Report on Patentability dated Jan. 10, 2008.
PCT/US2006/024752 International Report and Written Opinion dated Nov. 7, 2006.
PCT/US2007/076348 International Search Report and Written Opinion dated Jun. 20, 2008.
PCT/US2004/003528 International Search Report mailed Jul. 30, 2004, 6 pages.
Notice of Reasons of Rejection for Japanese Application No. 2008-518488, mailed Feb. 7, 2012.
Notice of Reasons of Rejection for Japanese Application No. 2008-518488, mailed Jul. 10, 2012.
Japanese Office Action, Apr. 15, 2013, Application No. 2011-039140, Decision of Rejection.
European Office Action, Mar. 26, 2013, Application No. 04708599.8.

* cited by examiner

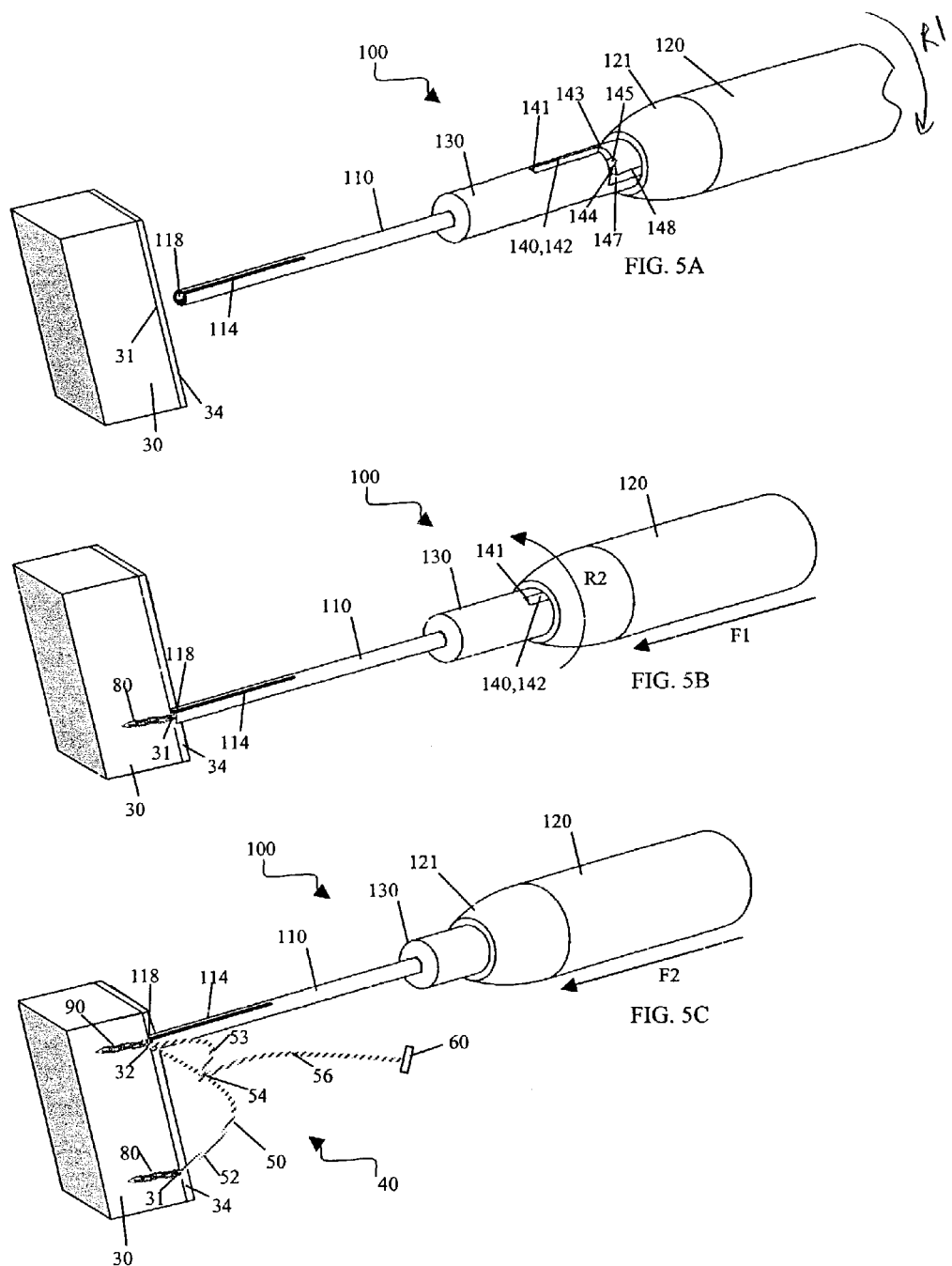

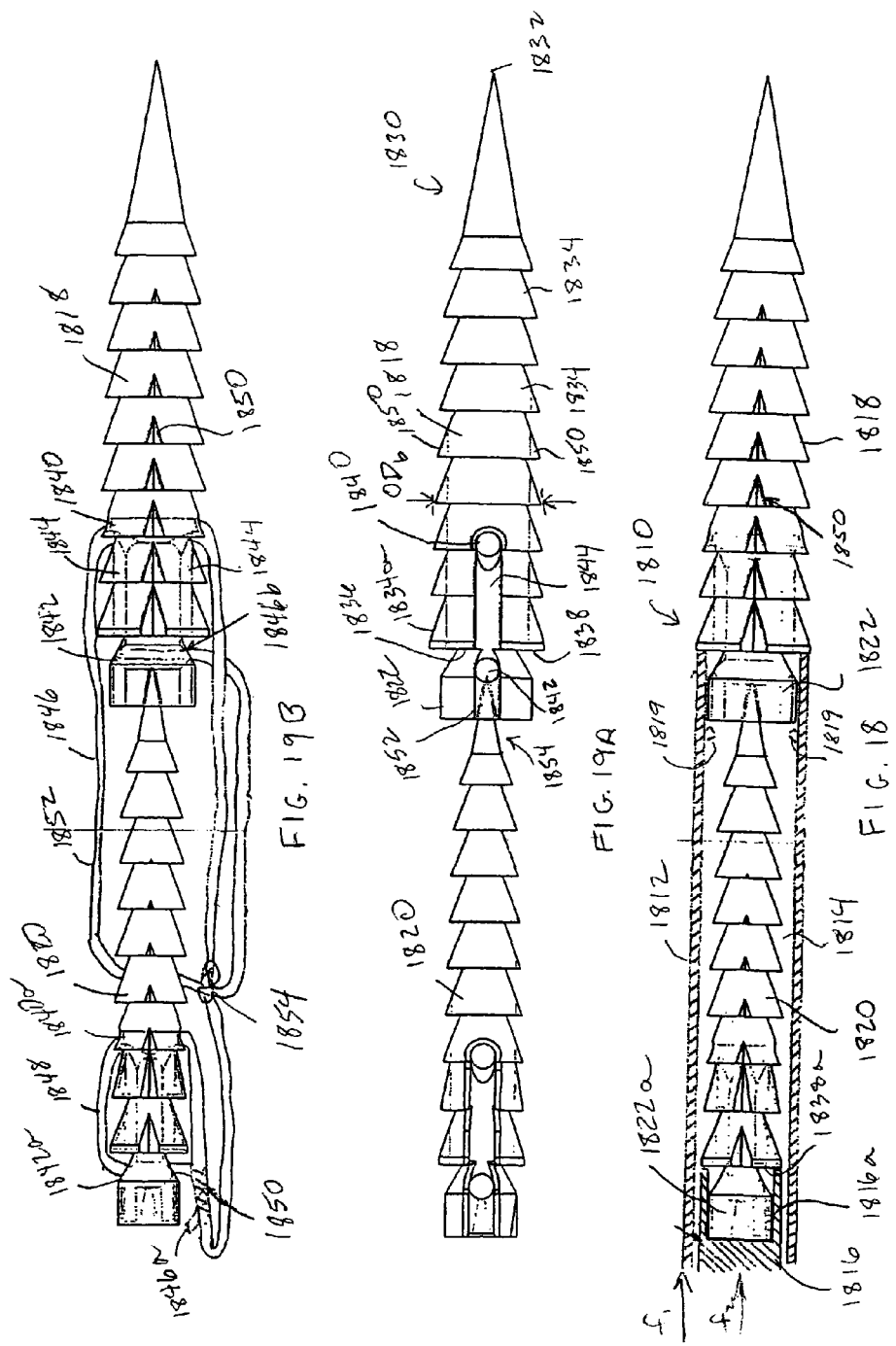

TISSUE ANCHOR AND INSERTION TOOL

This invention relates to tissue anchors and tools for inserting tissue anchors.

BACKGROUND

Soft tissue such as ligaments and tendons, after they have torn away from bone, can be reattached using suture. A surgeon inserts an anchor with an attached suture into the bone and ties the suture about the soft tissue to secure the soft tissue to the bone. It is known to use pound-in and screw-in type anchors. Tools for inserting pound-in type anchors generally include an outer tube in which the anchor is located, and an inner pusher tube for expelling the anchor from the tool. Tools for inserting screw-in type anchors generally have a tube that is somehow keyed to the anchor, typically by including a hexagonal-shaped end on the anchor and a hexagonal-shaped opening in the tube for receiving the end of the anchor, such that rotation of the tool acts to screw in the anchor.

SUMMARY

According to one aspect of the invention, a surgical tool includes a shaft for receiving implants. The shaft defines a non-linear track. The tool includes a deployment member movable along the track to deploy the implants.

Embodiments of this aspect of the invention may include one or more of the following features.

The track includes longitudinal and lateral sections. The deployment member includes a nub received in the track. The deployment member includes a handle and the nub extends from an inner surface of the handle. The deployment member includes a pusher for engaging the implants. The shaft defines a lumen for receiving the pusher.

The track defines a formation for releasably locking the deployment member. The formation is a concavity, and the deployment member includes a nub releasably received in the concavity.

The shaft is a cylindrical member and defines a lumen for receiving the implants. The shaft includes an adapter defining the track and a longitudinally extending member for receiving the implants. The surgical tool includes a second shaft coupled to the adapter and positioned alongside the longitudinally extending member. The surgical tool includes a hole forming member received by the second shaft and a lever coupled to the hole forming member for distally advancing the hole forming member relative to the second shaft. The adapter defines a second track for receiving the lever. Alternatively, a nub is received in the first track for advancing the hole forming member relative to the second shaft.

According to another aspect of the invention, a surgical tool includes implants and a shaft for receiving the implants. The shaft defines a non-linear track. The surgical tool includes a deployment member movable along the track to selectively deploy the implants.

Embodiments of this aspect of the invention may include a spacer disposed between two implants.

According to another aspect of the invention, a method includes advancing a shaft to a surgical site, the shaft housing implants, and moving a deployment member along a non-linear track defined by the shaft to deploy the implants into tissue at the surgical site.

According to another aspect of the invention, an implant includes a body, and a plurality of alternating threads and flutes helically arranged about the body such that the body rotates under a linear applied force. Each thread includes multiple barbs.

Embodiments of this aspect of the invention may include that the body defines a longitudinal passage.

According to another aspect of the invention, an implant includes a body having a distal end for pound-in advancement into tissue. The body includes a plurality of cone-shaped, stacked barbs, and a diameter of an outermost region of the barbs increases proximally.

Embodiments of this aspect of the invention may include a proximal break-away hub.

According to another aspect of the invention, a surgical tool includes a first member, a first implant coupled to the first member, a second member coupled to the first member, and a second implant coupled to the second member. The first implant has forward threads and the second implant has reverse threads.

Embodiments of this aspect of the invention may include one or more of the following features.

The surgical tool includes a suture joining the first and second implants. The first member defines a lumen and the second member is received within the lumen. The surgical tool includes a deployment element for advancing the second member relative to the first member.

According to another aspect of the invention, a surgical tool includes a first member, a first implant coupled to the first member, a second member coupled to the first member, and a second implant coupled to the second member. The first implant has threads for rotary advancement into tissue and the second implant is configured for pound-in advancement into tissue.

Embodiments of this aspect of the invention may include one or more of the following features.

The surgical tool includes a suture joining the first and second implants. The first member defines a lumen and the second member is received within the lumen. The surgical tool includes a deployment element for advancing the second member relative to the first member.

According to another aspect of the invention, a surgical tool includes a first member, a first implant coupled to the first member, a second member coupled to the first member, and a second implant coupled to the second member. The first and second implants are configured for pound-in advancement into tissue.

Embodiments of this aspect of the invention may include one or more of the following features.

The surgical tool includes a suture joining the first and second implants. The first member defines a lumen and the second member is received within the lumen. The surgical tool includes a deployment element for advancing the second member relative to the first member.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 5A-5C are diagrammatic illustrations of the insertion tool of FIG. 1 shown at various stages during deployment of suture anchors;

FIG. 18 is another embodiment of an insertion tool with suture anchors;

FIG. 19A is a side view of the suture anchors of FIG. 18;

FIG. 19B is a top view of the suture anchors of FIG. 18 shown with a suture coupled to the anchors.

DETAILED DESCRIPTION

Figure 1:
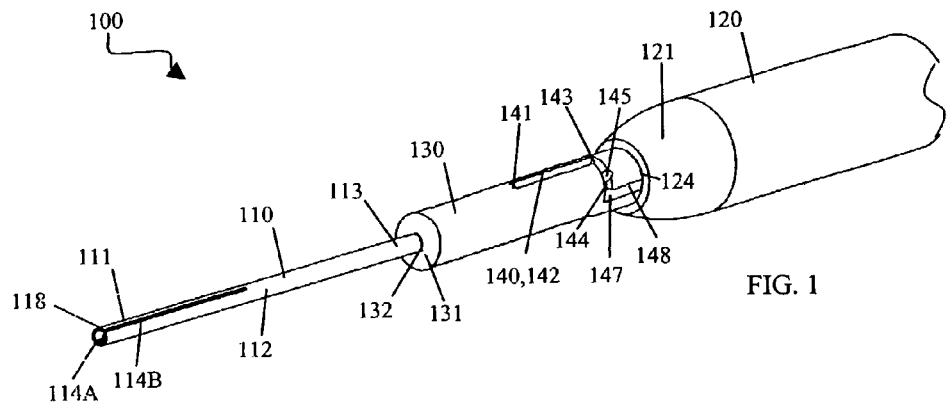
FIG. 1 is a perspective view of a suture anchor insertion tool.
Figure 2A:
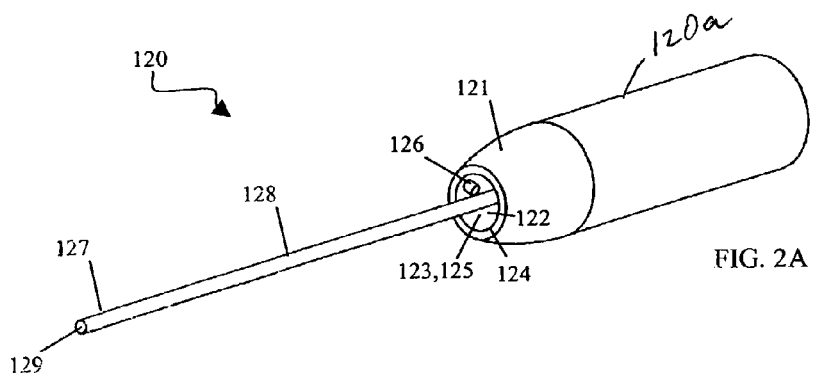
FIG. 2A is a perspective view of a handle of the suture anchor insertion tool of FIG. 1.

Referring to FIG. 1, an insertion tool 100 permitting arthroscopic insertion of two anchors coupled by a suture to, e.g., attach soft tissue to bone, includes an outer tubular member 110 for housing the two anchors, an adaptor 130 enabling controlled deployment of the anchors from outer tubular member 110, and an actuating handle 120 for deploying the anchors. Referring also to FIG. 2A, handle 120 has a nub 126 and adaptor 130 defines a guide track 140 that receives nub 126 such that movement of nub 126 along track 140 guides the deployment of the two anchors from outer tubular member 110.

Figure 2B:
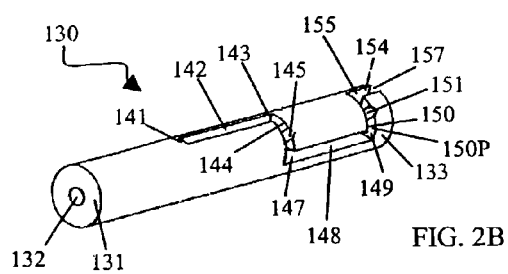
FIG. 2B is a perspective view of an adaptor of the suture anchor insertion tool of FIG. 1.
Figure 2C:
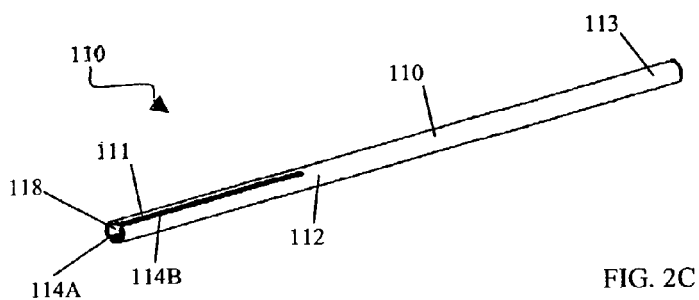
FIG. 2C is a perspective view of a member of the suture anchor insertion tool of FIG. 1.

Referring to FIGS. 1 and 2C, outer tubular member 110 has a proximal region 113 and a distal region 111. Distal region 111 has an anchor receiver 118 for receiving the anchors. Adaptor 130 has a distal face 131 defining a through bore 132 for receiving proximal region 113 of outer tubular member 110. Outer tubular member 110 has a wall 112 defining a pair of substantially parallel longitudinal slots 114A, 114B extending through wall 112 in distal region 111, for purposes described below.

Referring to FIGS. 2A and 2B, handle 120 includes a hand grip 120a and a plunger member 128. Hand grip 120a has a distal end 121 with a distal wall 124. Wall 124 defines a circular opening 122 into a conical chamber 123 bounded by an interior wall 125. Nub 126 extends radially inward from interior wall 125. Opening 122 and chamber 123 are dimensioned to receive a proximal end 133 of adaptor 130 such that nub 126 is located in track 140 to attain guided relative motion between handle 120 and adaptor 130. Plunger member 128 is received within adapter through bore 132 and within outer tubular member 110. Plunger member 128 has a distal region 127 terminating in a contact face 129 for engaging an anchor located within outer tubular member 110.

Referring particularly to FIG. 2B, guide track 140 extends from proximal end 133 along part of the length of adaptor 130. Guide track 140 is formed by a first longitudinal extent 154, a first lateral extent 150, a second longitudinal extent 148, a second lateral extent 144, and a third longitudinal extent 142. First longitudinal extent 154 opens at a hole 157 in proximal end 133 to allow nub 126 to enter track 140. First longitudinal extent 154 extends distally from hole 157 to a first junction 155 with first lateral extent 150. First lateral extent 150 includes a stop 151 that is dimensioned to releasably receive nub 126 to hinder relative movement of nub 126 along track 140. Stop 151 is a concave depression in the proximal wall 150P of lateral extent 150 with a radius of curvature slightly larger than the radius of nub 126. First lateral extent 150 extends laterally along the outer circumference of adaptor 130 from first junction 155 with first longitudinal extent 154 to a second junction 149 with second longitudinal extent 148. Second longitudinal extent 148 extends distally from second junction 149 to a third junction 147 with second lateral extent 144, and has a length of about 1 inch (normalized with respect to a received suture anchor). Second lateral extent 144 includes a stop 145 that is similar to stop 151, and extends laterally along the outer circumference of adaptor 130 from third junction 147 to a fourth junction 143 with third longitudinal extent 142. Third longitudinal extent 142 extends distally from fourth junction 143 to an end 141, and has a length of about 1 inch (normalized with respect to a received suture anchor). The lengths of second longitudinal extent 148 and third longitudinal extent 142 determine the insertion depth of the two anchors housed in member 110, as discussed further below.

Figure 3:
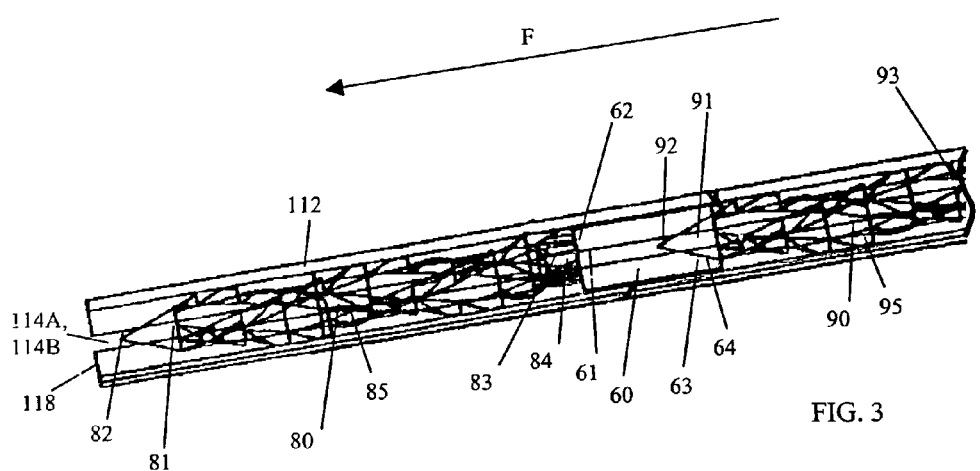
FIG. 3 is a hidden line view of a distal portion of the suture anchor insertion tool of FIG. 1.

Referring to FIG. 3, anchor receiver 118 of outer tubular member 110 receives two anchors 80, 90, e.g., pound-in anchors, arranged in a row. Anchors 80, 90 each include a distal end 81, 91 capped by a tip 82, 92 and a proximal end 83, 93 with a suture eyelet 84, 94 (FIG. 4), respectively. Tips 82, 92 are sufficiently robust to penetrate tissue, e.g., bone. Eyelets 84, 94 are dimensioned to pass at least one strand of suture for connecting the suture to anchors 80, 90, as discussed below in regard to FIG. 17. Anchors 80, 90 are lined by a series of barb threads 85, 95 for retaining anchor 80, 90 in the penetrated tissue, as discussed below in regard to FIGS. 14A-16.

Anchors 80, 90 are separated by a spacer 60 that is also inside outer tubular member 110. Spacer 60 has a distal end 61 with a contact face 62 and a proximal end 63 that defines a tip dock 64. Within tube wall 112, contact face 62 abuts proximal end 83 of anchor 80, and tip dock 64 receives tip 92 of anchor 90. Tip dock 64 is generally conical in shape to increase the contact area with tip 92 and prevent tip 92 from penetrating tip dock 64. Anchors 80, 90 and spacer 60 thus form a mechanical linkage capable of transmitting an expulsion force from anchor 90 to anchor 80 to insert anchor 80 into tissue, e.g., bone.

Figure 4:
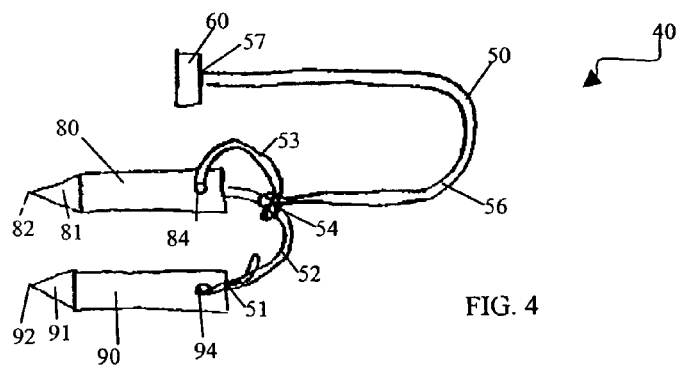
FIG. 4 is a perspective view of a suture anchor assembly.

Referring also to FIG. 4, an anchor assembly 40 is formed by anchors 80, 90 and spacer 60 joined by a suture 50. Suture 50 is retained in anchor receiver 118 inside outer tubular member 110 along with anchors 80, 90 and spacer 60. Suture 50 has a first knotted loop 51 that passes through eyelet 94 for joining suture 50 to anchor 90, and a first suture portion 52 that extends from eyelet 94 through eyelet 84. Suture 50 has a second portion 53 that exits eyelet 84 and is tied in a slip knot 54 with first suture portion 52. Suture 50 also includes a third suture portion 56 that exits slip knot 54 and extends to an end 57 joined to spacer 60. With the anchors loaded as shown in FIG. 3, suture runs along either side of anchor 90 with slip knot 54 positioned proximal of anchor 90. When a surgeon or other operator pulls on spacer 60, the length of first suture portion 52 is shortened. Slip knot 54 is a one-way knot in that the slip knot permits shortening of suture portion 52, but limits any tendency of suture portion 52 to lengthen.

In use, an operator positions insertion tool 100 with anchor receiver 118 oriented toward a selected surgical site 31 in a bone 30. Surgical site 31 is, e.g., a site where a soft tissue 34 is to be reattached to bone 30. Insertion tool 100 is preloaded with anchors 80, 90, spacer 60, and suture 50 with slip knot 54. Prior to use, nub 126 has been advanced through hole 157 along first longitudinal extent 154 and a portion of first lateral extent 150 of track 140 to stop 151 (FIG. 2B).

Referring to FIGS. 2B and 5A, the operator then advances anchor receiver 118 to contact surgical site 31 and presses handle 120 distally to release nub 126 from stop 151. The operator rotates handle 120 in the direction of arrow R1 to move nub 126 further along first lateral extent 150 to junction 149, where nub 126 enters longitudinal extent 148.

Referring also to FIG. 5B, the operator then applies an axial force F1 to handle 120, moving nub 126 distally along second longitudinal extent 148 and advancing plunger member 128 such that contact face 129 of plunger member 128 engages proximal end 93 of anchor 90 pushing anchor 90 distally. Tip 92 of anchor 90 in turn presses against tip dock 64 of spacer 60 which in turn presses against proximal end 83 of anchor 80 to push anchor 80 distally out of tubular member 110, causing tip 82 of anchor 80 to penetrate into bone 30 at site 31.

When nub 126 reaches the end of second longitudinal extent 148 at junction 147, the penetration of anchor 80 into bone 30 is completed. The operator then rotates handle 120 in the direction of arrow R2, moving nub 126 along a portion of second lateral extent 144 of track 140 to stop 145. The operator then releases the distally-directed pressure on handle 120 so that stop 145 receives nub 126 to hinder further relative movement between handle 120 and adaptor 130.

The operator then withdraws tool 100 from site 31, drawing suture 50 through slot 114 and spacer 60 and slip knot 54 out of anchor receiver 118. The operator then aligns anchor receiver 118 with a second surgical site 32, and presses handle 120 distally to release nub 126 from stop 145. The operator then rotates handle 120 in the direction of arrow R2 to move nub 126 further along second lateral extent 144 to junction 143, where nub 126 enters third longitudinal extent 142.

Referring to FIG. 5C, the operator applies a force F2 to handle 120 moving nub 126 distally along third longitudinal extent 142 such that contact face 129 of plunger member 128 pushes against proximal end 93 of anchor 90 pushing anchor tip 92 into bone 30 at site 32. Penetration proceeds until nub 126 reaches end 141, at which time anchor assembly 40 is fully deployed from insertion tool 100. The operator then removes insertion tool 100 from surgical site 32, pulls on spacer 60 to shorten suture portion 62 and thus hold soft tissue 34 to bone 30. Slip knot 54 acts to limit loosening of the suture.

Further embodiments are within the scope of the following claims.

Figure 6A:
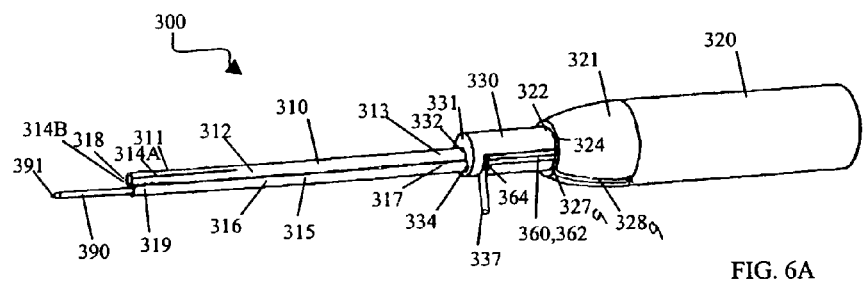
FIG. 6A is a perspective view of an alternative embodiment of a suture anchor insertion tool.
Figure 6C:
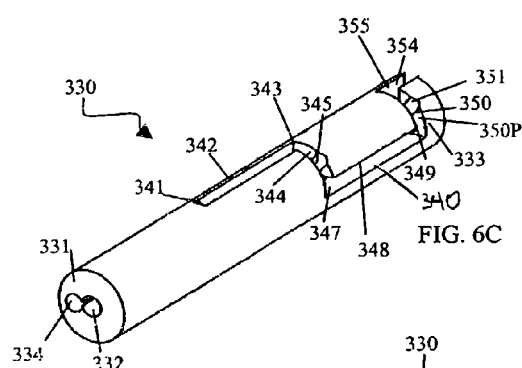
FIGS. 6C and 6D are other perspective views of the adaptor of the insertion tool of FIG. 6A.
Figure 6D:
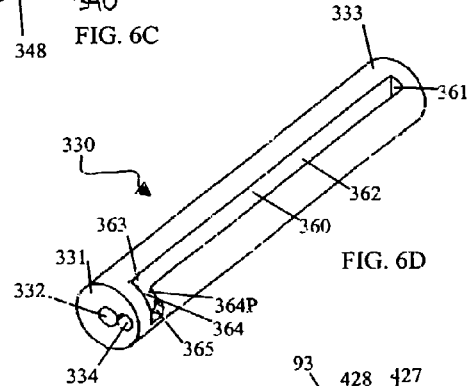

For example, referring to FIG. 6A, a suture anchor insertion tool 300 permitting arthroscopic insertion of two anchors coupled by a suture to, e.g., attach soft tissue to bone includes an outer tubular member 310 for housing the two anchors, an actuating handle 320 for deploying the anchors, a second tubular member 315 mounted side-to-side with member 310 housing a retractable awl 390 for punching a hole in bone, an actuating lever 337 for controlling awl 390, and an adaptor 330 enabling controlled deployment of the anchors from member 310 and the awl from member 315. Referring also to FIGS. 6C and 6D, adaptor 330 defines a first guide track 340 and a second guide track 360. Guide track 340 guides the deployment of the two anchors from member 310 in the same manner as described above with reference to guide track 140. Guide track 360 guides the extension and retraction of awl 390 by lever 337. Lever 337 is coupled to awl 390, e.g., by a press fit, welding or soldering.

Figure 7:
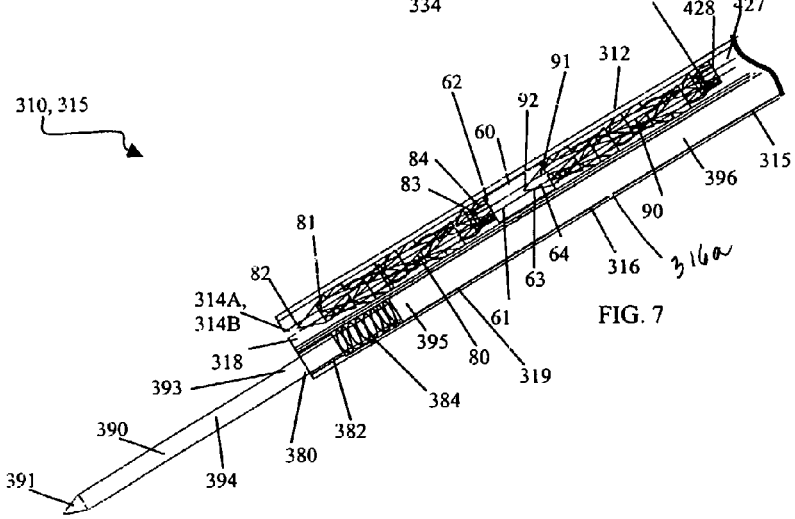
FIG. 7 is a hidden line view of a distal portion of the suture anchor insertion tool of FIG. 6A.

Outer tubular member 310 has a proximal end 313 and a distal end 311 with an anchor receiver 318 for receiving the suture anchors. Tubular member 310 has a wall 312 with a pair of substantially parallel longitudinal slots 314A, 314B extending therethrough at distal end 311. Referring also to FIG. 7, anchor receiver 318 of member 310 receives anchors 80, 90 in the same manner as described above with reference to anchor receiver 118.

Member 315 has a wall 316 defining a lumen 316a for receiving retractable awl 390. Member 315 has a proximal end 317 and a distal end 319. Distal end 317 has an inner radial lip 382 defining a hole 380. Awl 390 has an extensible portion 394 dimensioned to pass through hole 380, and a body portion 396. Extensible portion 394 ends in an awl tip 391. Body portion 396 is dimensioned to catch on inner radial lip 382 such that body portion 396 cannot extend through hole 380. Member 315 also includes a compression spring 384 that acts between a distal end 395 of body portion 396 and radial lip 382 to retract extensible portion 394 into lumen 316a when lever 337 is moved proximally, as discussed further below.

Figure 6B:
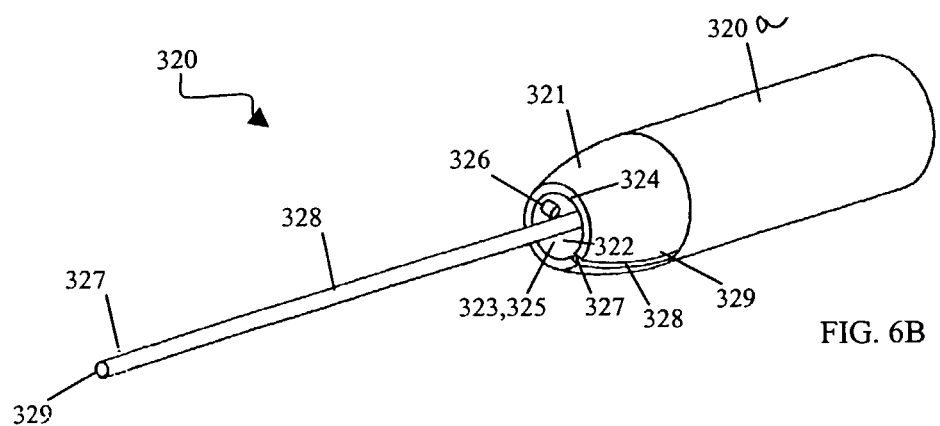
FIG. 6B is a perspective view of an adaptor of the insertion tool of FIG. 6A.

Referring to FIGS. 6A and 6B, handle 320 includes a hand grip 320a and a plunger member 328. Hand grip 320a has a distal end 321 with a distal wall 324. Wall 324 defines a circular opening 322 into a conical chamber 323 bounded by an interior wall 325. Nub 326 extends radially inward from interior wall 325. Opening 322 and chamber 323 are dimensioned to receive proximal end 333 of adaptor 330 and maintain nub 326 in track 340 to attain guided relative motion between handle 320 and adaptor 330 for deploying two anchors from member 310. Distal end 321 also defines a longitudinal slit 328a that extends proximally from a distal opening 327a at wall 324. Longitudinal slit 328a is angularly positioned relative to nub 326 such that, when nub 326 is received in longitudinal extent 342 of adapter 330, slit 328 is radially aligned with second guide track 360. Plunger member 328 is dimensioned to slidably fit within member 310. Plunger member 328 has a distal region 327 terminating in a contact face 329 for engaging an anchor located within outer tubular member 310.

Referring to FIGS. 6A, 6C, and 6D, adaptor 330 has a proximal end 333 and a distal face 331 defining a pair of through bores 332, 334. Plunger member 128 is received within adapter through bore 332. Proximal end 313 of tubular member 310 is received within through bore 332, and a proximal end 317 of tubular member 315 is received within through bore 334. Guide tracks 340, 360 extend along opposite sides of adaptor 330.

Guide track 340 is formed by a first longitudinal extent 354, a first lateral extent 350, a second longitudinal extent 348, a second lateral extent 344, and a third longitudinal extent 342. First longitudinal extent 354 opens at a hole 357 in proximal end 333 to allow nub 326 to enter track 340. First longitudinal extent 354 extends distally from hole 357 to a first junction 355 with first lateral extent 350. First lateral extent 350 includes a stop 351 that is dimensioned to releasably receive nub 326 to hinder relative movement of nub 326 along track 340. Stop 351 is a concave depression in the proximal wall 350P of lateral extent 350 with a radius of curvature slightly larger than the radius of nub 326. First lateral extent 350 extends laterally along the outer circumference of adaptor 330 from first junction 355 with first longitudinal extent 354 to a second junction 349 with second longitudinal extent 348. Second longitudinal extent 348 extends distally from second junction 349 to a third junction 347 with second lateral extent 344, and has a length of about 1 inch (normalized with respect to a received suture anchor). Second lateral extent 344 includes a stop 345 that is similar to stop 351, and extends laterally along the outer circumference of adaptor 330 from third junction 347 to a fourth junction 343 with third longitudinal extent 342. Third longitudinal extent 342 extends distally from fourth junction 343 to an end 341, and has a length of about 1 inch (normalized with respect to a received suture anchor). The lengths of second longitudinal extent 348 and third longitudinal extent 342 determine the insertion depth of the two anchors housed in member 310, as discussed further below.

Guide track 360 is formed by a longitudinal extent 362 and a lateral extent 364. Longitudinal extent 362 extends distally from a proximal side 361 to a junction 363 with lateral extent 364. Lateral extent 364 extends laterally along the outer circumference of adaptor 330 from junction 363 to a stop 365. Stop 365 is dimensioned to releasably receive lever 337 to hinder relative movement of lever 337 along track 360 and maintain extensible portion 394 of awl 390 extended through hole 380. Stop 363 is a concave depression in the proximal wall 364P of lateral extent 364 with a radius of curvature slightly larger than the radius of lever 337 in track 360.

Figure 8A:
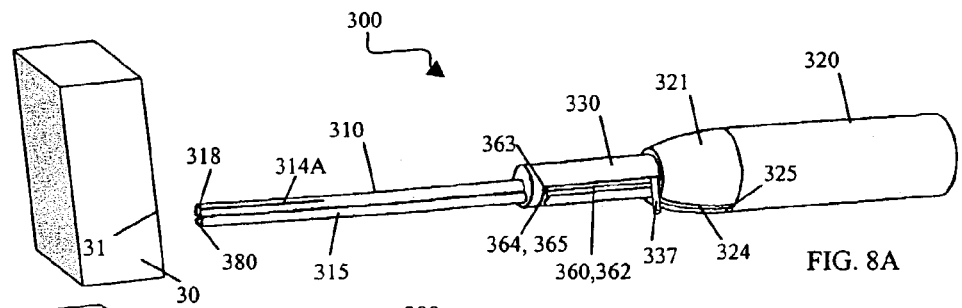
FIG. 8A-8F are diagrammatic illustrations of the insertion tool of FIG. 6A shown at various stages during deployment of suture anchors.

Referring to FIG. 8A, in use, an operator positions insertion tool 300 with members 310, 315 oriented toward a selected surgical site 31 in a bone 30. Surgical site 31 is, e.g., a site where a soft tissue 34 is to be reattached to bone 30. Insertion tool 300 is preloaded with anchors 80, 90, spacer 60, and suture 50 with a slip knot. Nub 326 has been advanced through hole 357 along first longitudinal extent 354 and a portion of first lateral extent 350 of track 340 to stop 351 of FIG. 6C. Awl lever 337 is positioned proximally in track 360 such that the awl is retracted.

Figure 8B:
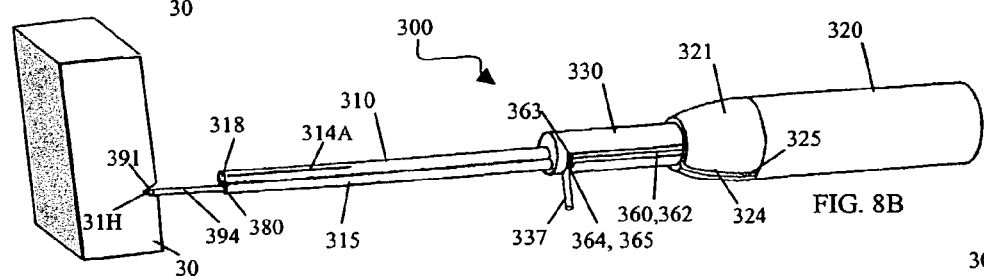

Referring to FIG. 8B, the operator advances lever 337 distally along longitudinal extent 362 of track 360, advancing the awl out of member 315. When lever 337 reaches junction 363, the operator moves lever 337 laterally along lateral portion 364 into stop 365 which receives lever 337 and maintains the awl in the extended position. The operator uses the awl to make a hole 31H through the soft tissue into bone 30 at surgical site 31.

After hole 31H is formed, the operator moves lever 337 laterally along lateral portion 364 out of stop 365 toward junction 363. At junction 363, the operator releases lever 337 and spring 384 (FIG. 7) pushes lever 337 proximally to retract extensible portion 394 of the awl into member 315.

Figure 8C:
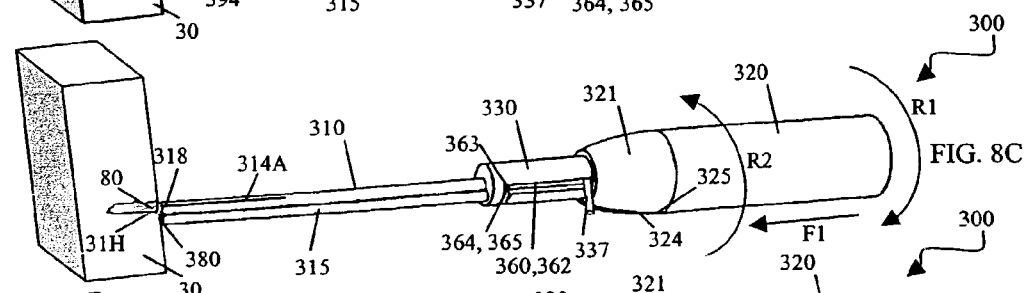

Referring to FIG. 8C, the operator then aligns anchor receiver 318 with hole 31H and presses handle 320 distally to release nub 326 from stop 351. The operator rotates handle 320 in the direction of arrow R1 to move nub 326 further along first lateral extent 350 to junction 349, where nub 326 enters longitudinal extent 348. The operator applies a force F1 to handle 320, moving nub 326 distally along second longitudinal extent 348 and advancing contact face 329 of plunger member 328 (shown in FIG. 6B) against proximal end 93 of anchor 90 to deploy anchor 80 as described above. The operator then rotates handle 320 in the direction of arrow R2, moving nub 326 along a portion of second lateral extent 344 of track 340 to stop 345 (shown in FIG. 6C). The operator then releases the distally-directed pressure on handle 320 so that stop 345 receives nub 326 to hinder further relative movement between handle 320 and adaptor 330. Lever 337 has been moved distally in track 360 by the action of handle 320, though the awl is still fully located within member 315.

Figure 8D:
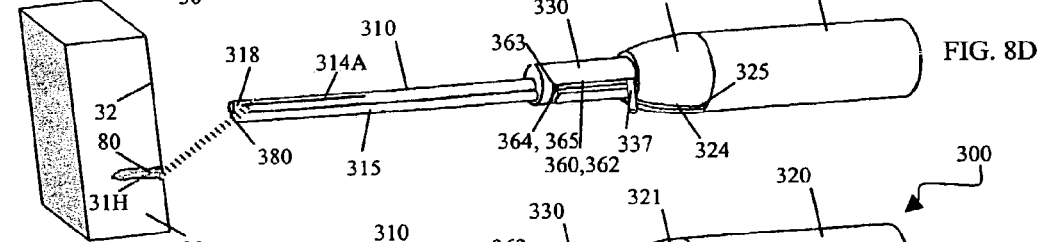

Referring to FIG. 8D, the operator then withdraws tool 300 from hole 31H, drawing suture 50 through one of slots 314A, 314B and spacer 60 out of anchor receiver 318. The operator then orients members 310, 315 toward a second selected surgical site 32.

Figure 8E:
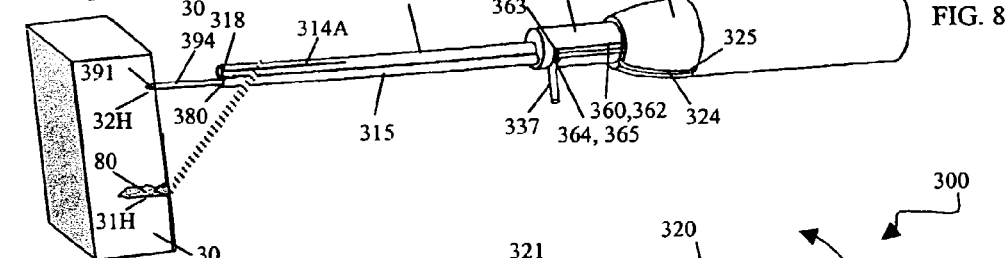

Referring to FIG. 8E, the operator advances lever 337 distally along longitudinal extent 362 of track 360, advancing the awl out of member 315. When lever 337 reaches junction 363, the operator moves lever 337 laterally along lateral portion 364 into stop 365 which receives lever 337 and maintains the awl in the extended position. The operator uses the awl to make a hole 32H through the soft tissue into bone 30 at surgical site 32.

After hole 32H is formed, the operator moves lever 337 laterally along lateral portion 364 out of stop 365 toward junction 363. At junction 363, the operator releases lever 337 and spring 384 (FIG. 7) pushes lever 337 proximally to retract extensible portion 394 of the awl into member 315.

Figure 8F:
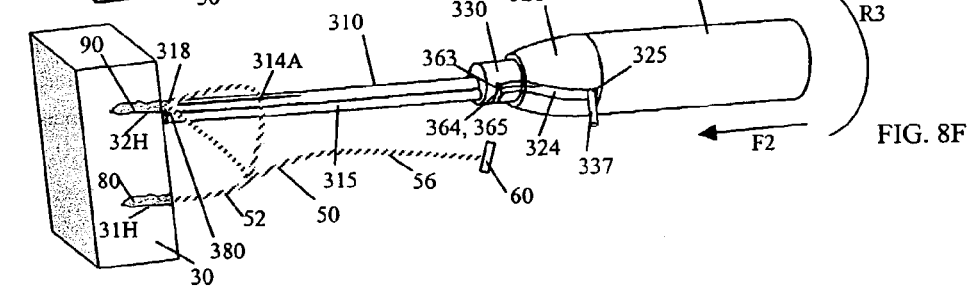

Referring to FIG. 8F, the operator then aligns anchor receiver 318 with hole 32H and presses handle 320 distally to release nub 326 from stop 345. The operator rotates handle 320 in the direction of arrow R3 to move nub 326 further along second lateral extent 344 to junction 343, where nub 326 enters third longitudinal extent 342. The operator applies a force F2 to handle 320, moving nub 326 distally along third longitudinal extent 342 and advancing contact face 329 against proximal end 93 of anchor 90 to deploy anchor 90, as described above. During the advancement of handle 320, lever 337 enters track 342 of handle 320. The operator then moves insertion tool 300 away from hole 32H, and grasps spacer 60 to tighten suture portion 62 and hold a soft tissue 34 to bone 30.

Figure 9A:
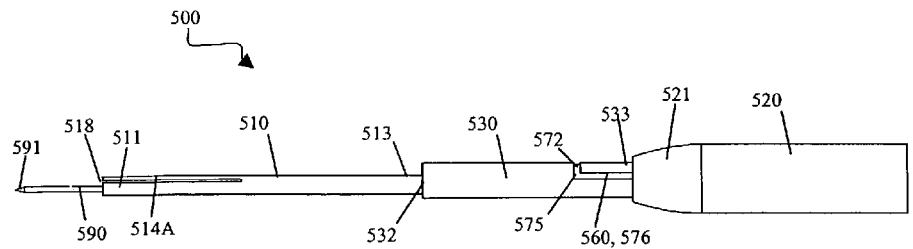
FIG. 9A is a perspective view of another alternative embodiment of a suture anchor insertion tool.

Referring to FIG. 9A, another suture anchor insertion tool 500 permits arthroscopic insertion of two anchors coupled by a suture to, e.g., attach soft tissue to bone. Insertion tool 500 includes an outer tubular member 510 that receives the two anchors and a retractable awl 590. Awl 590 has a tip 591 for forming a hole in bone. Tool 500 includes an actuating handle 520 for deploying the anchors and extending awl 590, and an adaptor 530 having a guide track 560 enabling controlled deployment of the anchors and awl 590 from member 510.

Figure 9B:
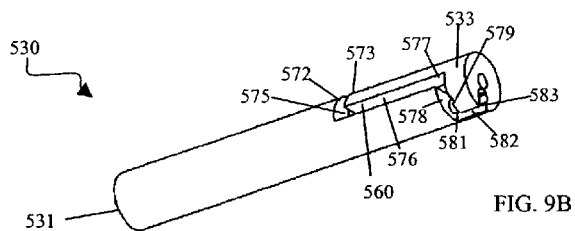
FIG. 9B is a perspective view of an adaptor of the insertion tool of FIG. 8A.
Figure 9C:
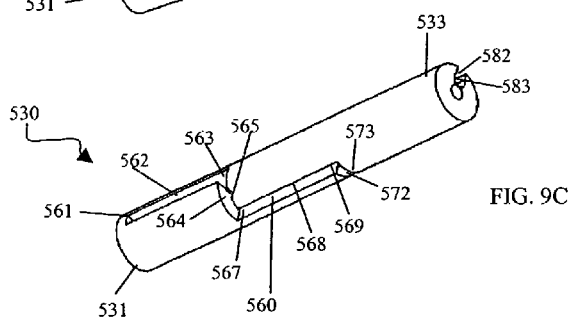
FIG. 9C is another perspective view of the adaptor of the insertion tool of FIG. 8A.
Figure 9D:
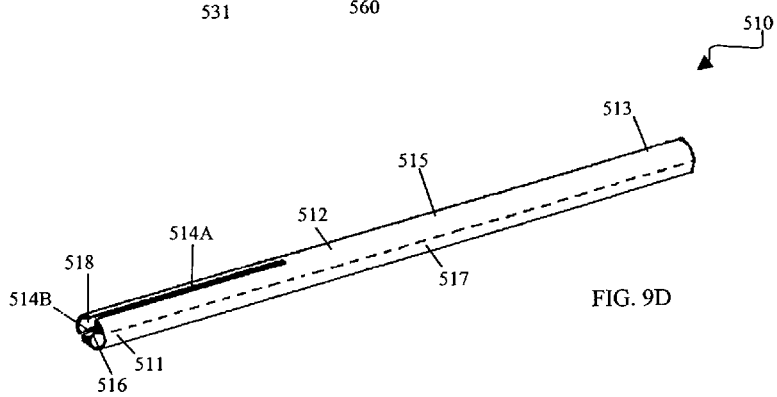
FIG. 9D is a perspective view of a member of the suture anchor insertion tool of FIG. 9A.

Referring to FIGS. 9A and 9D, member 510 has a proximal end 513 and a distal end 511 with an anchor receiver 518 for receiving the suture anchors. Member 510 has an outer circumferential wall 512 and an inner wall 516 that divides the interior of member 510 into a plunger channel 515 and an awl channel 517. Anchor receiver 518 is part of plunger channel 515. Wall 512 defines a pair of substantially parallel longitudinal slots 514A, 514B that extend into anchor receiver 518. Anchor receiver 518 receives anchors 80, 90 as described above. Awl 590 is spring loaded as shown in FIG. 7.

Figure 9E:
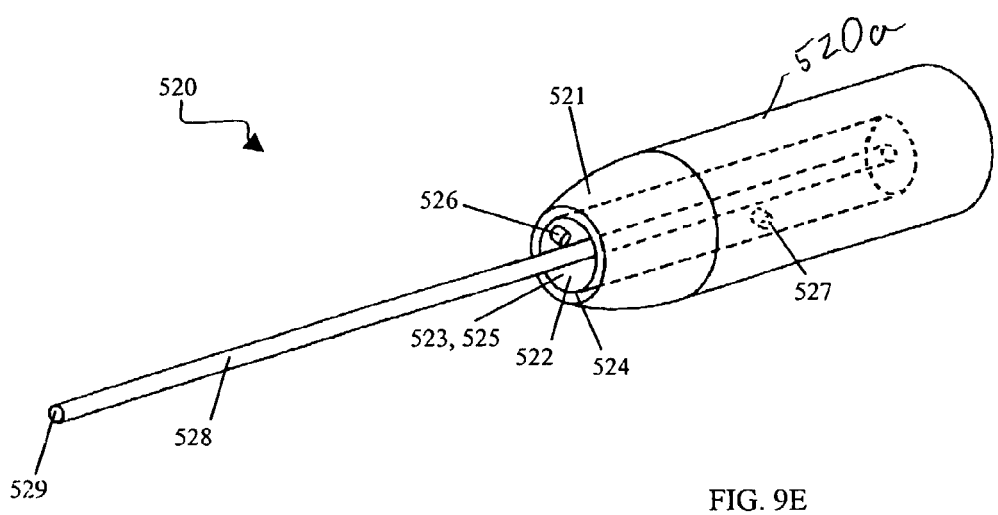
FIG. 9E is a perspective view of a handle of the suture anchor insertion tool of FIG. 9A.

Referring to FIGS. 9A and 9E, handle 520 includes a hand grip 520a and a plunger member 528. Handle 520 has a distal end 521 bounded by a distal wall 524. Wall 524 defines a circular opening 522 into a conical chamber 523 bounded by an interior wall 525. Opening 522 and chamber 523 are dimensioned to receive proximal end 533 of adaptor 530 to attain guided relative motion between handle 520 and adaptor 530. A pair of nubs 526, 527 extend radially inward from interior wall 525. Nubs 526, 527 are relatively positioned to be received by track 560 to enable controlled deployment of the anchors and awl 590 from member 510. Plunger member 528 is dimensioned to slidably fit within plunger channel 515 of member 510. Plunger member 528 terminates in a contact face 529.

Referring to FIGS. 9A, 9B, and 9C, adaptor 530 defines a single guide track 560 that guides the deployment of two anchors and extension and retraction of awl 590 from member 510. Adaptor 530 has a proximal end 533 and a distal face 531 and defines a through bore hole 532 that receives proximal end 513 of tubular member 510 and plunger 528. Guide tracks 560 wraps around the outer circumference of adaptor 530.

Guide track 540 is formed by a first longitudinal extent 582, a first lateral extent 578, a second longitudinal extent 576, a second lateral extent 372, a third longitudinal extent 568, a third lateral extent 564, and a fourth longitudinal extent 562. First longitudinal extent 582 opens at a hole 583 in proximal end 533 to allow nubs 926, 927 to enter track 560, as discussed further below. First longitudinal extent 354 extends distally from hole 583 to a first junction 581 with first lateral extent 578. First lateral extent 578 includes a stop 579 that is dimensioned to releasably receive nubs 926, 927 to hinder relative movement of nubs 926, 927 along track 560. Stop 579 is a concave depression with a radius of curvature slightly larger than the radius of nub 326. First lateral extent 578 extends laterally along the outer circumference of adaptor 530 from first junction 581 with first longitudinal extent 582 to a second junction 577 with second longitudinal extent 576. Second longitudinal extent 576 extends distally from second junction 577 to a third junction 575 with second lateral extent 572. Second longitudinal extent 576 has a length of about 1 inch (normalized with respect to a received suture anchor). Second lateral extent 572 includes a stop 573 that is similar to stop 579. Second lateral extent 572 extends laterally along the outer circumference of adaptor 530 from third junction 575 to a fourth junction 569 with third longitudinal extent 568. Third longitudinal extent 568 extends distally from fourth junction 569 to a fifth junction 567 with third lateral extent 564. Third longitudinal extent 568 has a length of about 1 inch (normalized with respect to a received suture anchor). Third lateral extent 564 includes a stop 565 that is similar to stop 579. Third lateral extent 564 extends laterally along the outer circumference of adaptor 530 from fifth junction 567 to a sixth junction 563 with fourth longitudinal extent 562. Fourth longitudinal extent 562 extends distally from sixth junction 563 to an end 561, and has a length of about 1 inch (normalized with respect to a received suture anchor).

Figure 10A:
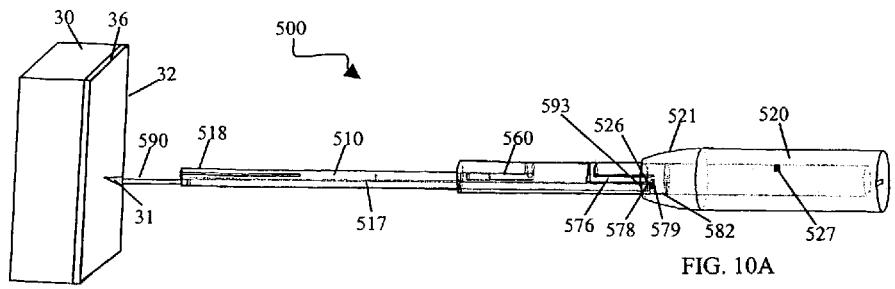
FIG. 10A-10E are diagrammatic illustrations of the insertion tool of FIG. 8A shown at various stages during deployment of suture anchors.

Referring to FIG. 10A, in use, an operator positions insertion tool 500 with awl 590 oriented toward a selected surgical site 31 in a bone 30. Surgical site 31 is, e.g., a site where a soft tissue 34 is to be reattached to bone 30. Insertion tool 500 is preloaded with anchors 80, 90, spacer 60, and suture 50 with a slip knot. Nub 526 has been advanced through hole 583 along first longitudinal extent 582 and a portion of first lateral extent 578 of track 560 to stop 579 of FIG. 9B. Nub 526 contacts a proximal end 593 of awl 590 to extend and maintain awl 590 out of awl channel 517. The operator uses awl 590 to form a hole 311H in bone 30 and soft tissue 36.

Figure 10B:
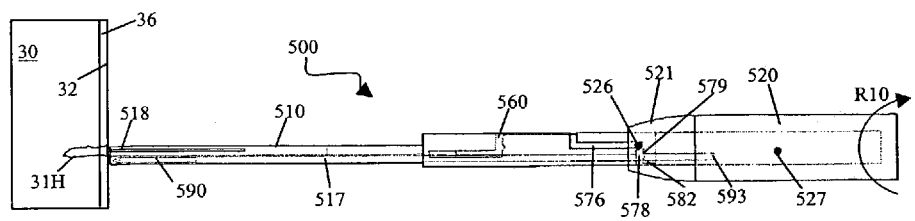

Referring to FIG. 10B, after forming hole 31H, the operator rotates handle 520 in the direction of arrow R10 to move nub 526 out of stop 579 and into longitudinal extent 576. This moves nub 526 out of contact with a proximal end 593 of awl 590 to allow a spring (not shown) to retract awl 590 into awl channel 517, as described above. The operator then positions anchor receiver 518 at hole 31H in preparation for insertion of anchor 90.

Figure 10C:
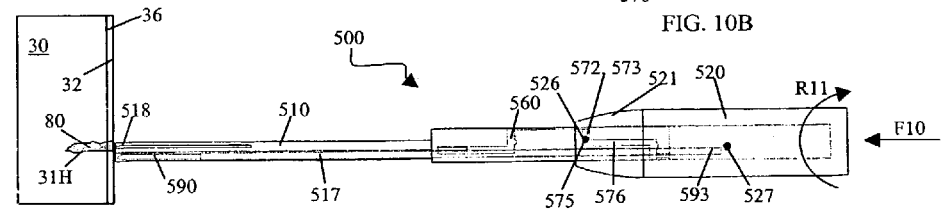

Referring to FIG. 10C, the operator applies a force F10 to handle 520 moving nub 526 distally along longitudinal extent 576 and advancing plunger member 528 to deploy anchor 80. The operator then rotates handle 520 in the direction of arrow R11, moving nub 526 along a portion of second lateral extent 572 of track 560 to stop 573 (shown in FIGS. 9B and 9C). The operator then releases the distally-directed pressure on handle 520 so that stop 573 receives nub 526 to hinder further relative movement between handle 520 and adaptor 530.

Figure 10D:
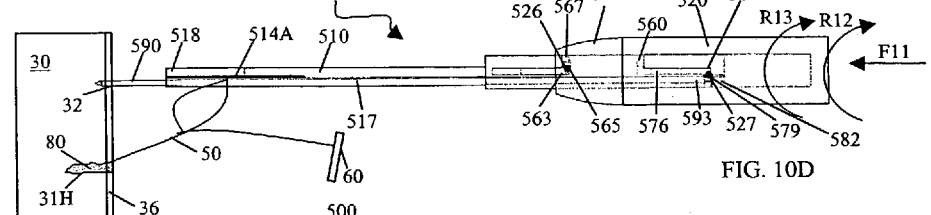

Referring to FIG. 10D, the operator then withdraws tool 500 from hole 311H, drawing suture 50 through one of slots 514A, 514B. The operator then rotates handle 520 in the direction of arrow R12 to move nub 526 out of stop 573 and to junction 569 of lateral extent 572 and longitudinal extent 568. The rotation of handle 520 in the direction of arrow R12 also brings nub 527 into contact with the distal end 593 of awl 590. The operator then pushes distally on handle 520 to advance nub 526 distally along longitudinal extent 568 and to advance nub 527 into longitudinal extent 582. The advancement of nub 526 along longitudinal extent 568 pushes spacer 60 out of anchor receiver 518. The advancement of nub 527 into longitudinal extent 582 extends awl 590 out of awl channel 515. Once nub 526 reaches junction 567 and nub 527 reaches junction 581, the operator then rotates handle 520 in the direction of arrow R13 to move nub 527 into stop 565 in lateral extent 564 and nub 526 into stop 579 in lateral extent 578. The operator then uses awl 590 to form a hole 32H in the bone at surgical site 32.

Figure 10E:
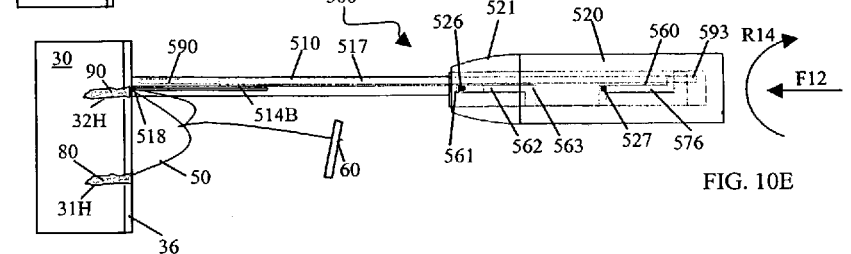

Referring to FIG. 10E, after forming hole 32H, the operator rotates handle 520 in the direction of arrow R14. This rotation moves nub 527 out of stop 579 and into longitudinal extent 576, and moves nub 526 out of stop 565 and into longitudinal extent 562. This moves nub 526 out of contact with a proximal end 593 of awl 590 to allow the spring to retract awl 590 into awl channel 517. The operator then positions anchor receiver 518 at hole 31H in preparation for insertion of anchor 90. The operator then applies a force F12 to handle 520 moving nub 526 distally along longitudinal extent 562 and nub 527 distally along longitudinal extent 576, and advancing plunger member 528 to deploy anchor 90. The operator then moves insertion tool 500 away from hole 32H, and grasps spacer 60 to tighten suture portion 62 and hold a soft tissue 34 to bone 30.

Figure 11:
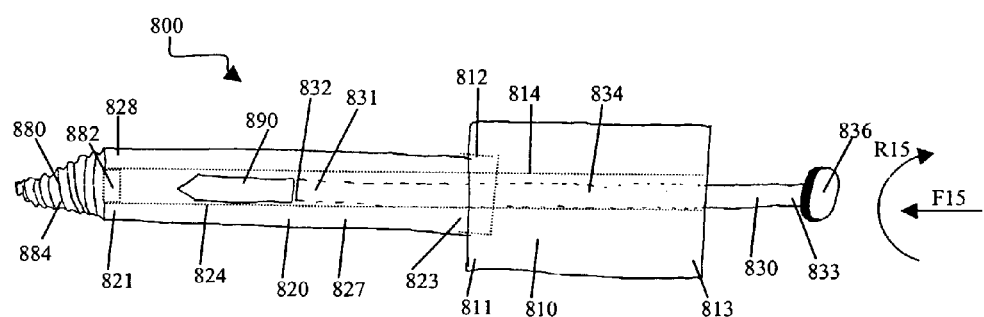
FIG. 11 is a perspective view of another alternative embodiment of a suture anchor insertion tool.

Referring to FIG. 11, another suture anchor insertion tool 800 permits arthroscopic insertion of two anchors coupled by a suture to, e.g., attach soft tissue to bone. Insertion tool 800 includes a handle 810, an outer tubular member 820 for housing the two anchors, and a plunger member 830 for inserting one of the two anchors, as discussed below.

Handle 810 has a distal end 811 and a proximal end 813 and defines an interior channel 814 extending therebetween that receives plunger member 830. Distal end 811 of handle 810 defines a cutout portion 812 for receiving a proximal end 823 of member 820 in, e.g., a compression fit.

Member 820 has a distal end 821 and proximal end 823, and has a wall 827 defining an axial channel 824 extending from proximal end 823 to distal end 821. When proximal end 823 of member 820 is received in cutout portion 812 of handle 810, axial channel 824 of member 820 communicates with interior channel 814 of handle 810 to form a passage for plunger member 830. Distal end 821 of member 820 includes a suture anchor receiver 828 for non-rotatably mating with a first suture anchor 880. Channel 824 is, e.g., hex-shaped in the region of anchor receiver 828, and anchor 880 includes a mating portion 882 that is, e.g., a male hex head to couple suture anchor 880 to suture anchor receiver 828 for combined rotation. Anchor 880 is held in the channel by, e.g., a friction fit or an interference fit. Suture anchor 880 also includes a thread 884 for facilitating torsional insertion of suture anchor 880 into bone.

Plunger member 830 includes an elongate rod portion 834 with a distal end 831 defining a contact face 832 and a proximal end 833 terminating in a knob 836. Rod portion 834 is dimensioned to slide within axial channel 824 of member 820 and axial channel 814 of handle 810.

A second suture anchor 890 is received in axial channel 824 of member 820 and is dimensioned to slide therein. Suture anchor 890 is designed for pound-in insertion into bone as discussed in, e.g., FIGS. 14A-16B. Suture anchors 880, 890 are, e.g., joined by a suture with a slip knot and separated by a spacer as illustrated in FIG. 4.

In use, an operator inserts suture anchor 880 into a first surgical site by contacting suture anchor 880 to the site and applying a rotational torque R15 to handle 810. The operator then contacts suture anchor 890 to a second surgical site and applies an axial force F15 to knob 836 to drive plunger member 830 distally and deploy suture anchor 890 distally out of channel 824 and into the second surgical site.

Figure 12:
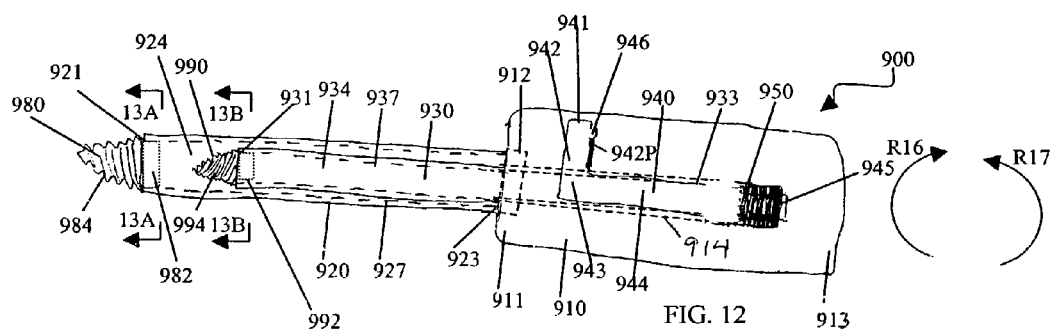
FIG. 12 is a perspective view of another alternative embodiment of a suture anchor insertion tool.
Figure 13A:
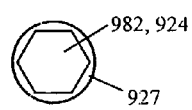
FIG. 13A is a cross-sectional view taken along lines 13A-13A of FIG. 12.
Figure 13B:
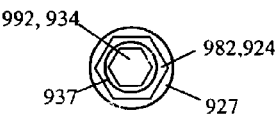
FIG. 13B is a cross-sectional view taken along lines 13B-13B of FIG. 12.

Referring to FIGS. 12, 13A, and 13B, another suture anchor insertion tool 900 permits arthroscopic insertion of two anchors coupled by a suture to, e.g., attach soft tissue to bone. Insertion tool 900 includes a handle 910 defining a guide slot 940, an outer tubular member 920 having a first anchor receiver 921 for receiving the first suture anchor 980, and a plunger member 930 having a second anchor receiver 931 for receiving the second suture anchor 990. Plunger member 930 is slidably received inside member 920 and is guided by guide slot 940 for inserting second suture anchor 990 into bone.

Handle 910 has a distal end 911 and a proximal end 913 and defines an interior channel 914 for receiving plunger member 930. Distal end 911 of handle 910 defines a cutout portion 912 for receiving a proximal end 923 of member 920 in, e.g., a compression fit.

Guide slot 940 extends through handle 910 to communicate with channel 914. Guide slot 940 includes a distal lateral extent 942 and a proximally extending longitudinal extent 944. Lateral extent 942 extends laterally from an end 941 to a junction 943 with longitudinal extent 944. Lateral extent 942 includes a stop 946 defined in a proximal wall 942P of slot 942. Longitudinal extent 944 extends longitudinally along handle 910 from junction 943 to a proximal stop 945.

Member 920 has a distal end 921 and a proximal end 923, and a wall 927 defining an axial channel 924 extending from proximal end 823 to distal end 921. When proximal end 923 of member 920 is received in cutout portion 912 of handle 910, axial channel 924 of member 920 communicates with interior channel 914 of handle 910 to form a passage for plunger member 930. Distal end 921 of member 920 includes suture anchor receiver 928 for non-rotatably mating with first suture anchor 980 having a mating portion 982, as described above with reference to FIG. 11. Suture anchor 980 also includes a thread 984 for facilitating torsional insertion of suture anchor 980 into bone.

Plunger member 930 has a distal end 931 and a proximal end 933, and a wall 937 defining an axial channel 934 extending from proximal end 933 to distal end 931. Plunger member 930 is dimensioned to slide within axial channel 924 of member 920 and interior channel 914 of handle 910. Distal end 921 of plunger member 930 includes a suture anchor receiver 938 for non-rotatably mating with second suture anchor 990 having a mating portion 992, such as with hex couplings as described above. Suture anchor 990 also includes a thread 994 for facilitating torsional insertion of suture anchor 990 into bone. Anchors 980 and 990 are oppositely threaded, for example, thread 984 facilitates torsional insertion of suture anchor 980 into bone when handle 910 is rotated in the direction of arrow R16, whereas thread 994 facilitates torsional insertion of suture anchor 990 into bone when handle 910 is rotated in the direction of arrow R17.

Proximal end 933 of plunger member 930 is joined to an actuating button 950 by, e.g., epoxy. Button 950 is slidable within guide slot 940 to extend distal end 931 of plunger member 930 out of channel 924 in member 920.

In use, an operator advances tool 800 to a first surgical site and inserts suture anchor 980 into the bone by rotating handle 910 in the direction of arrow R16. The operator then withdraws insertion tool 900 away from the first surgical site, releasing anchor 980, and advances button 950 distally along longitudinal extent 944 to advance plunger member 930 extending suture anchor 990 distally beyond distal end 921 of member 920. When button 950 reaches junction 943, the operator advances button 950 laterally within lateral extent 942 and into stop 946 to maintain suture anchor 990 beyond distal end 921 of member 920. The operator then deploys suture anchor 990 at second surgical site by rotating handle 910 in the direction of arrow R17. The opposite rotation used to deploy suture anchor 990 removes windup of the suture that may have occurred during insertion of the first anchor 980.

Figure 14A:
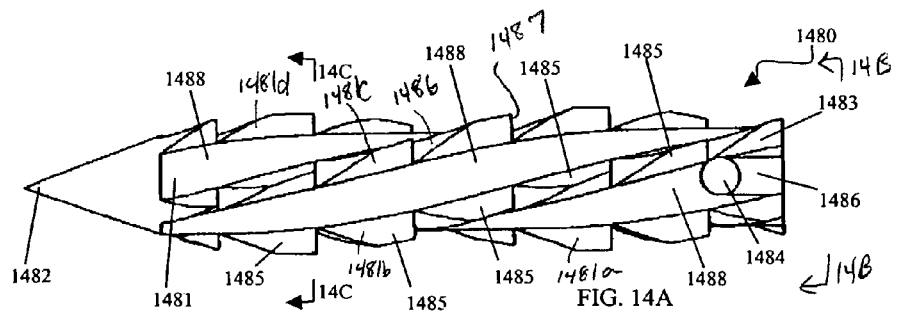
FIG. 14A is a perspective view of a suture anchor.
Figure 14B:
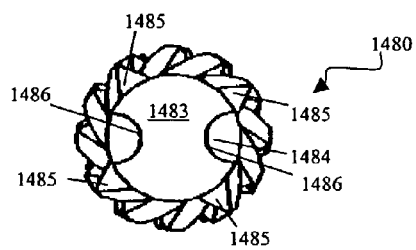
FIG. 14B is an end on view of the suture anchor of FIG. 14A.
Figure 14C:
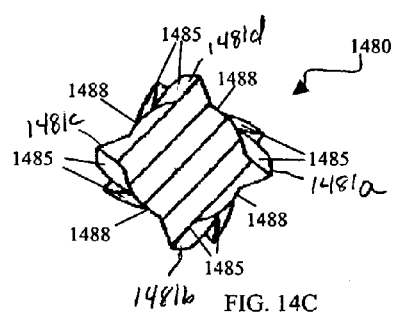
FIG. 14C is a cross-sectional view taken along lines 14C-14C of the suture anchor of FIG. 14A.

Referring to FIGS. 14A-14C, a pound-in suture anchor 1480 that rotates during insertion into tissue is generally rod-shaped and includes a distal end 1481 capped by a tip 1482 and a proximal end 1483 with a lateral suture eyelet 1484. Tip 1482 is sufficiently robust to penetrate tissue, e.g., bone. Eyelet 1484 is recessed from the outer circumference of suture anchor 1480 by a pair of recesses 1486 and is dimensioned to pass at least one strand of suture.

The outer circumference of anchor 1480 has four helical rows 1481a-1481d of barbed threads 1485. Each helical row has the same pitch of, e.g., about 2 mm, and is separated from neighboring helical rows by smooth helical flutes 1488. The helical rows 1481a-1481d act to cause anchor 1480 to rotate when an axial pound-in force is applied to the anchor to aid in insertion and retention of the anchor in bone. Barbed threads 1485 have distal tapers 1486 and proximal ledges 1487. Tapers 1486 aid in insertion of the anchor in bone, and ledges 1487 aid in retaining the anchor in bone. Anchor 1480 can be used as the pound-in type anchor of any of the embodiments described above.

Figure 15A:
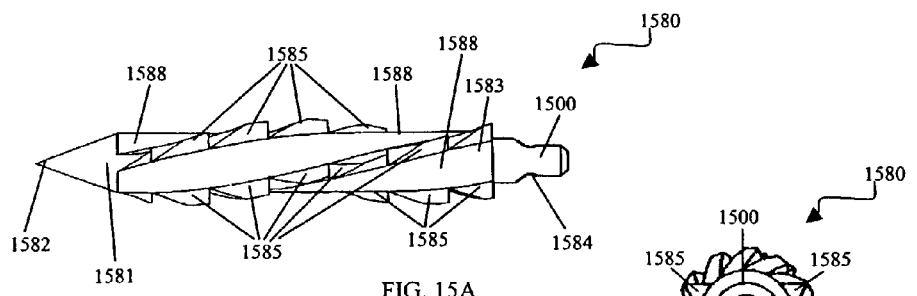
FIG. 15A is a perspective view of another suture anchor.
Figure 15C:
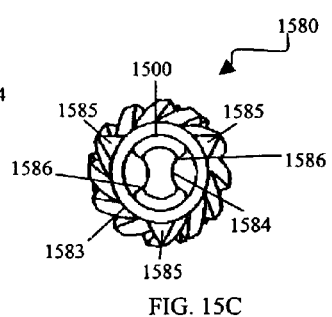
FIG. 15C is a cross-sectional view taken along lines 15C-15C of the suture anchor of FIG. 15A.
Figure 15B:
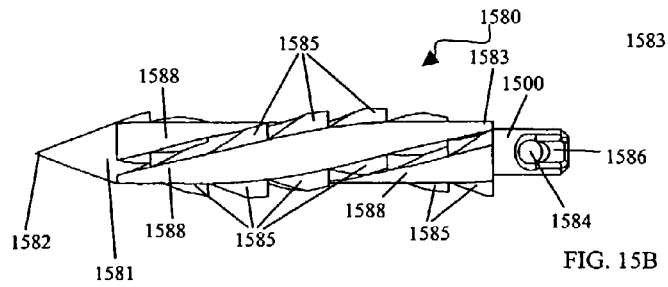
FIG. 15B is another perspective view of the suture anchor of FIG. 15A.

Referring to FIGS. 15A-15C, another embodiment of a pound-in type suture anchor 1580 that rotates during insertion into tissue includes a distal end 1581 capped by a tip 1582 and a proximal end 1583 capped by a proximal protrusion 1500 with a lateral suture eyelet 1584. Eyelet 1584 is recessed from the outer circumference of tip 1582 by a pair of recesses 1586 and is dimensioned to pass at least one strand of suture. As discussed above with reference to FIG. 14A, anchor 1580 has three helical rows of barbed threads 1585 separated by smooth helical flutes 1588.

Figure 16A:
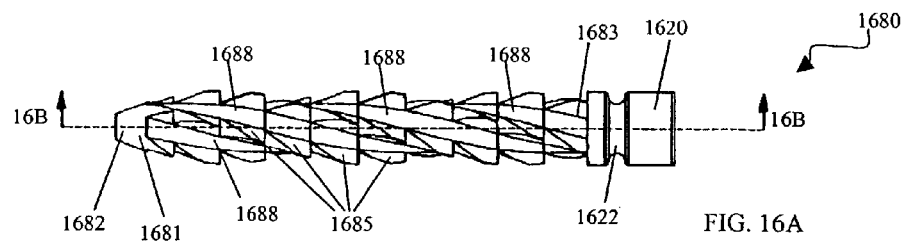
FIG. 16A is a perspective view of another suture anchor.
Figure 16B:
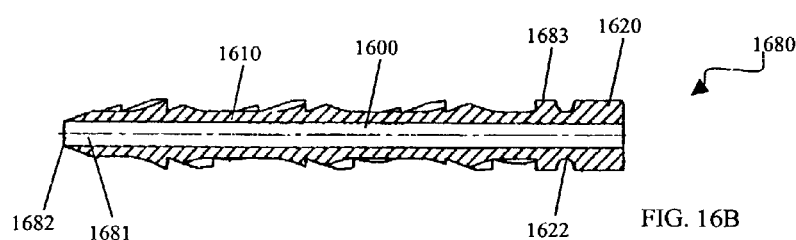
FIG. 16B is cross-sectional view taken along lines 16B-16B of the suture anchor of FIG. 16A.

Referring to FIGS. 16A and 16B, another embodiment of a pound-in type suture anchor 1680 that rotates during insertion into tissue includes a distal end 1681 capped by a blunt tip 1682 and a proximal end 1683 capped by a proximal tubular protrusion 1620. Protrusion 1620 is banded by a circumferential annular depression 1622 for tying a suture to suture anchor 1680, as discussed below with reference to FIG. 17A. Tip 1682 is blunt and is suitable for insertion, e.g., into a predrilled hole in bone or other tissue. Anchor 1680 has an annular wall 1610 defining an interior longitudinal channel 1600 that extends from distal end 1681 to proximal end 1683. Longitudinal channel 1600 receives a guidewire or other orienting member to aid in guiding anchor 1680 to the bone hole. As discussed above with reference to FIG. 14A, the outer circumference of anchor 1680 has four helical rows of barbed threads 1685 separated by smooth helical flutes 1688.

Figure 17A:
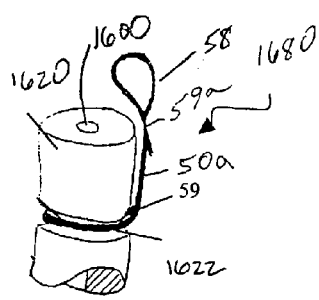
FIGS. 17A-17F are perspective views of links between suture anchors and sutures.

FIGS. 17A-17F illustrate various ways of coupling suture to a suture anchor. Referring to FIG. 17A, to couple suture 50 to suture anchor 1680 of FIG. 16A, one end of a length of suture 50a is looped around suture anchor 1680 within depression 1622, and secured by a knot 59, e.g., a heat sealed Chinese knot. The other end of suture 50a is formed into a loop 58 and secured by a knot 59a, e.g., a heat sealed Chinese knot. Loop 58 advantageously provides a good pulley surface for coupling suture 50 to anchor 1680.

Figure 17B:
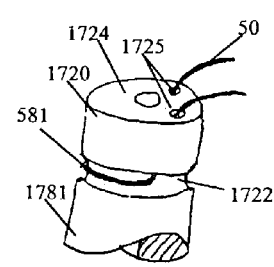

Referring to FIG. 17B, a suture anchor 1781 includes a proximal tubular protrusion 1720 banded by a circumferential annular depression 1722 for receiving suture 50. Tubular protrusion 1720 defines a pair of longitudinal channels 1725 that extend from a proximal face 1724 of the anchor to circumferential annular depression 1722 for receiving suture 50. Suture 50 passes from proximal face 1724 through longitudinal channel 1725, loops around annular depression 1722, and then returns past proximal face 1724 through longitudinal channel 1725.

Figure 17C:
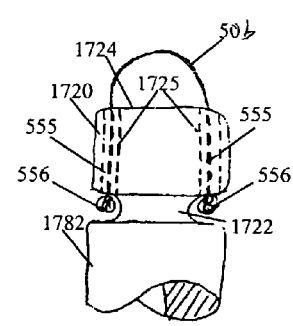

Referring to FIG. 17C, a suture anchor 1782 includes a proximal protrusion 1720 banded by a circumferential annular depression 1722, and defines a pair of longitudinal holes 1725 that extend from a proximal face 1724 of the anchor to circumferential annular depression 1722. Holes 1725 are located at opposite edges of protrusion 1720. A length of suture 50b has a pair of ends 555 that each pass through one longitudinal channel 1725 and terminate in a retaining knot 556 located in annular depression 1722 to form a pulley.

Figure 17D:
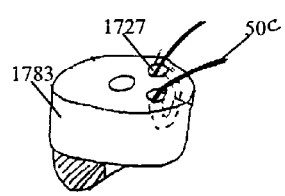
Figure 17E:
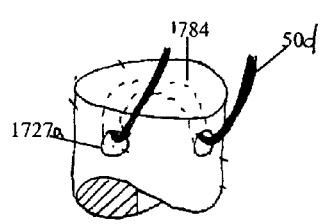

Referring to FIG. 17D, a suture anchor 1783 defines a channel 1727 through which suture 50c is threaded. One end of the suture can be fixed to the other suture, e.g., with a Chinese knot 59 (FIG. 17A) to form a loop with the other end of the suture extending from the knot, or the two ends of suture can be knotted together to form a pulley. Likewise, referring to FIG. 17E, a suture anchor 1784 defines a channel 1727a through which suture 50d is threaded and tied to form a loop or pulley.

Figure 17F:
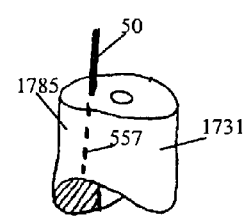

Referring to FIG. 17F, a suture anchor 1785 includes a suture portion 557 that is encased, e.g., during molding of suture anchor 1785, in proximal end 1731 of the anchor to couple suture 50 to suture anchor 1784. The coupling methods of FIGS. 17B, 17C, 17D and 17F all have the advantage that no suture extends beyond the diameter of the anchor.

Referring to FIG. 18, an anchor insertion assembly 1810 includes an outer tubular member 1812 defining a lumen 1814, and an inner member 1816 received within lumen 1814. Assembly 1810 includes first and second suture anchors 1818, 1820. Anchor 1818 has a proximal break-off hub 1822 received within lumen 1814, and anchor 1820 is received within lumen 1814 proximal of anchor 1818. Anchors 1818, 1820 are of the pound-in type. Application of an axial force, $f_1$, to outer tubular member 1812 is used to implant anchor 1818 into tissue, and application of an axial force, $f_2$, to inner member 1816 advances inner member 1816 relative to outer member 1812 to deploy anchor 1820.

Referring to FIGS. 19A and 19B, anchor 1818 has a distal end 1830 that tapers to a sharp point 1832, and a series of stacked, truncated cone shaped elements 1834. Each element 1834 tapers proximally to a larger outer diameter, with the base outer diameter, $OD_b$, of each element 1834 being larger than the element 1834 immediately distal thereof. Hub 1822 is coupled to proximal element 1834a by a thin section 1836 that allows hub 1822 to be broken off from element 1834a by application of lateral or tortional (e.g., twisting) force applied by outer member 1812 (FIG. 18). Hub 1822 has a smaller outer diameter than the base outer diameter of section 1834a such that a ledge 1838 is defined by section 1834a against which the axial force of outer tubular member 1812 can be applied to anchor 1818.

Anchor 1818 defines two through holes 1840, 1842 and a channel 1844 extending axially between each pair of through holes for receiving suture 1846. Each element 1834 defines two grooves 1850 that resist any tendency of anchor 1818 to twist during advancement into tissue. (Alternatively, grooves 1850 may be replaced by raised ribs for added strength.) Hub 1822 has a proximal opening 1852 that receives a distal end 1854 of anchor 1820. Anchor 1820 is identical in design to anchor 1818, with the exception of having a smaller outer diameter. The smaller outer diameter permits anchor 1820 to fit within outer tubular member lumen 1814. While anchor 1820 is shown in the figure as smaller than anchor 1818, it need not be smaller (e.g. anchors 1818 and 1820 may be the same length and/or diameter). Inner member 1816 (FIG. 18) is a solid cylindrical member with a distal notch 1816a for receiving break-off hub 1822a of anchor 1820. Inner member 1816 acts against a ledge 1838a of anchor 1820 to advance anchor 1820 into tissue.

Referring particularly to FIG. 19B, from a first suture end 1846a, suture 1846 extends through hole 1842a in anchor 1820, then through hole 1840a in anchor 1820 to form a loop 1848 secured by a Chinese knot 1850. From knot 1850, suture 1846 extends distally to anchor 1818 and through hole 1840 to form a loop 1852 secured by a slip knot 1854. From knot 1854, suture 1846 extends to hole 1842, within which a second end 1846b of suture 1846 is fixed. While not shown in FIG. 19B, suture 1846 resides within channels 1844 between holes 1842 and 1844, and between holes 1842a and 1844a, such that in use, the suture located within the tissue remains within the outer diameter of the anchors.

Figure 20:
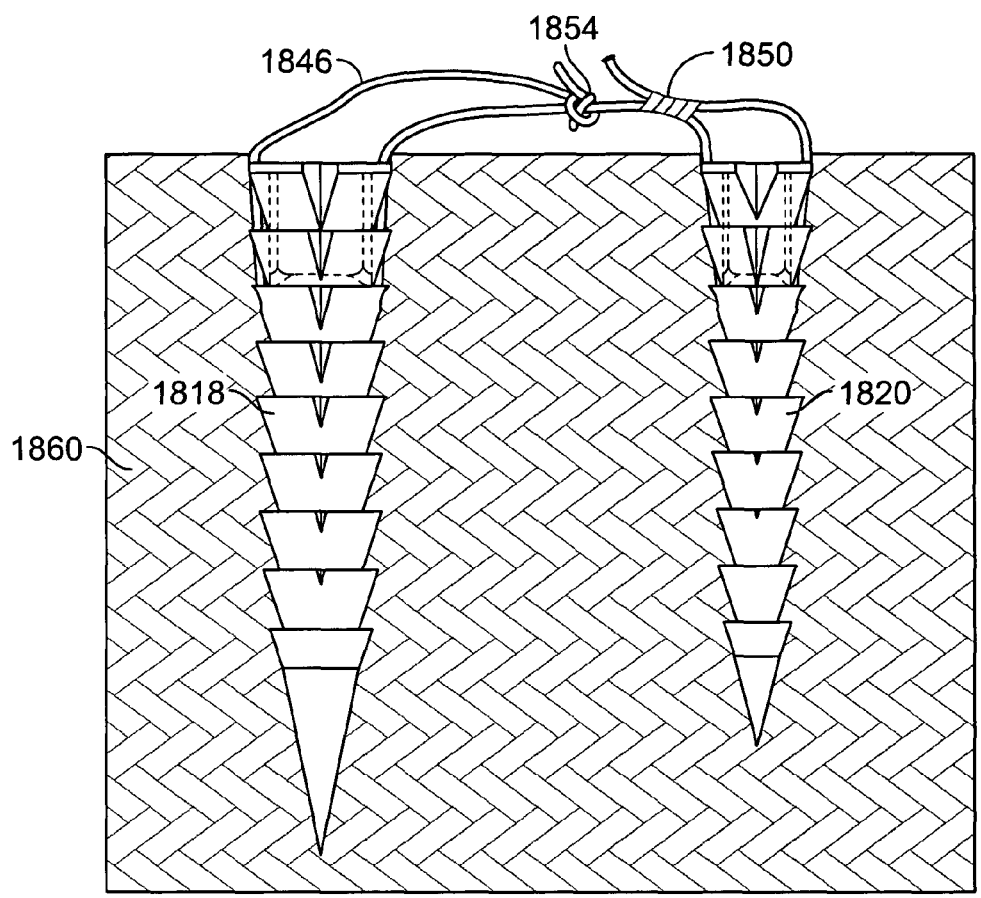
FIG. 20 shows the suture anchors of FIG. 18 deployed in tissue.

Referring to FIG. 20, in use, the operator pounds anchor 1818 into bone 1860. (Alternatively, a hole may be preformed for the anchor, e.g., by drilling.) The engagement of the distal end of outer tube 1812 against the proximal end of anchor 1818 transmits the driving forces to anchor 1818. Alternatively, if anchor 1818 were reduced in diameter to, e.g., that of anchor 1820, the driving forces may be transmitted by the engagement of one or more protrusions (e.g., punch 1819, shown in phantom in FIG. 18) against a proximal end of hub 1822. Punch 1819 must permit anchor 1820 and inner member 1816 to pass, of course.

Due to the break-off nature of hub 4822, outer tubular member 1812 does not need advance as far into bone 1860 to implant anchor 1818 as compared to an anchor having a hub that would need to be advanced into the bone. This has the advantage of limiting possible tissue damage that can occur when the end of an anchor delivery device is advanced into the bone to advance the hub into the bone. By applying a lateral or tortional force to outer tubular member 1812, the operator breaks off hub 1822 from the remainder of anchor 1818. Grooves 1850 resist anchor 1818 rotating in the bone as the break-off force is applied. This is particularly useful if the operator employs tortional force due to, e.g., limited space at the surgical site. Hub 1822 remains attached to suture end 1846b such that hub 1822 does not become a loose body.

The operator then advances inner member 1816 relative to outer member 1812 to deploy anchor 1820 at a second location in bone 1860. (Alternatively, a hole may be preformed for the anchor, e.g., by drilling.) The operator then applies a lateral or tortional force to inner member 1816 to break off hub 1822a. By then pulling on hub 1822 of anchor 1818, slip knot 1854 is moved along suture 1846 to tighten suture 1846, thus, e.g., functioning to securely reattach soft tissue to bone 1860. The operator then trims suture 1846 near slip knot 1854 and removes hub 1822. Hub 1822a is attached to inner member 1816 (e.g. with adhesive or by a press fit) so that it does not fall out of outer tubular member 1812 into the surgical site.

A number of embodiments of the invention have been described. Nevertheless, it will be understood that various modifications may be made without departing from the spirit and scope of the invention. For example, surgical site 31 may be a predrilled hole in bone 30. The various embodiments of pound-in anchors can include a break-off hub. Accordingly, other embodiments are within the scope of the following claims.

What is claimed is:

1. A surgical tool comprising:
    an outer tubular member, an adaptor coupled to the outer tubular member, and a handle coupled to the adapter, the adaptor having a non-circumferential, continuous guide track formed along a length of the adaptor, the handle having a nub disposed within the guide track, the adaptor disposed within an opening of the actuator handle such that the opening completely encircles a portion of the adaptor;
    a first implant and a second implant housed within the outer tubular member, the second implant proximal to the first implant; and
    a deployment element coupled to the handle and received within the outer tubular member for advancement of the first and second implants into tissue,
    wherein a partial advancement of the nub along the guide track by the handle deploys the first implant from the outer tubular member and another partial advancement of the nub along the guide track by the handle deploys the second implant from the outer tubular member.

2. The surgical tool of claim 1 further comprising a suture joining the first and second implants.

3. The surgical tool of claim 1, wherein the nub is disposed within the opening of the handle.

4. A surgical tool comprising:
    an outer tubular member, an adaptor coupled to the outer tubular member, and a handle coupled to the adaptor, the adaptor including a non-circumferential, continuous guide track formed along a length of the adaptor, the handle having a nub disposed within the guide track, the adaptor disposed within an opening of the handle such that the opening completely encircles a portion of the adaptor;
    a first implant coupled to the outer tubular member for deployment at a first surgical site;
    a second implant coupled to the outer tubular member and located proximal to the first member, for deployment at a second surgical site spaced from the first surgical site; and
    a deployment element coupled to the handle and received within the outer tubular member for advancement of the first and second implants into tissue,
    wherein a partial advancement of the nub along the guide track by the handle deploys the first implant from the outer tubular member and another partial advancement of the nub along the guide track by the handle deploys the second implants from the outer tubular member.

5. The surgical tool of claim 4 further comprising a suture joining the first and second implants.

6. A surgical tool comprising:
    an outer tubular member, an adaptor coupled to the outer tubular member, and a handle coupled to the adaptor, the adaptor including a non-circumferential, continuous guide track formed along a length of the adaptor, the handle having a nub disposed within the guide track;
    a first implant coupled to the outer tubular member for deployment at a first surgical site;
    a second implant coupled to the outer tubular member and located proximal to the first member, for deployment at a second surgical site spaced from the first surgical site; and
    a deployment element coupled to the handle and received within the outer tubular member for advancement of the first and second implants into tissue,
    wherein the adaptor is disposed within a circular opening of the handle completely encircling a portion of the adaptor.

7. The surgical tool of claim 6, wherein the nub is disposed within an opening of the handle.

8. A surgical tool comprising:
    an outer tubular member, an adaptor coupled to the outer tubular member, and a handle coupled to the adaptor, the adaptor including a non-circumferential, continuous guide track formed along a length of the adaptor, the handle having a nub disposed within the guide track;
    a first implant and a second implant housed within the outer tubular member, the second implant proximal to the first implant; and
    a deployment element coupled to the handle and received within the outer tubular member for advancement for the first and second implants into tissue,
    wherein the adaptor is disposed within a circular opening of the handle, the handle completely encircling a portion of the adaptor.

9. A surgical tool comprising:
    an outer tubular member, an adaptor coupled to the outer tubular member, and a handle coupled to the adaptor, the adaptor including a non-circumferential, continuous guide track formed along a length of the adaptor, the handle having a nub disposed within the guide track, the adaptor disposed within an opening of the handle such that the opening completely encircles a portion of the adaptor;

a first implant and a second implant housed within the outer tubular member, the second implant proximal to the first implant; and a deployment element coupled to the handle and received within the adaptor and the outer tubular member for advancement of the first and second implants into tissue, wherein a partial advancement of the nub along the guide track by the handle deploys the first implant from the outer tubular member and another partial advancement of the nub along the guide track by the handle deploys the second implants from the outer tubular member.

10. The surgical tool of claim 9, wherein the nub is disposed within the opening of the handle.

* * * * *